US008628938B2

(12) United States Patent
Ono et al.

(10) Patent No.: US 8,628,938 B2
(45) Date of Patent: Jan. 14, 2014

(54) POLYNUCLEOTIDE ENCODING UDP-GLUCURONYL TRANSFERASE

(75) Inventors: Eiichiro Ono, Osaka (JP); Akio Noguchi, Osaka (JP); Yuko Fukui, Osaka (JP); Masako Mizutani, Osaka (JP)

(73) Assignee: Suntory Holdings Limited, Osaka (JP)

( * ) Notice: Subject to any disclaimer, the term of this patent is extended or adjusted under 35 U.S.C. 154(b) by 581 days.

(21) Appl. No.: 12/678,161

(22) PCT Filed: Sep. 29, 2008

(86) PCT No.: PCT/JP2008/067613
§ 371 (c)(1),
(2), (4) Date: May 12, 2010

(87) PCT Pub. No.: WO2009/047992
PCT Pub. Date: Apr. 16, 2009

(65) Prior Publication Data
US 2010/0323402 A1    Dec. 23, 2010

(30) Foreign Application Priority Data

Oct. 12, 2007  (JP) ................................ 2007-267050
Mar. 17, 2008  (JP) ................................ 2008-067185

(51) Int. Cl.
  *C12P 21/06*  (2006.01)
(52) U.S. Cl.
  USPC ........... 435/69.1; 435/6; 435/193; 435/320.1; 435/252
(58) Field of Classification Search
  None
  See application file for complete search history.

(56) References Cited

U.S. PATENT DOCUMENTS

| | | | | |
|---|---|---|---|---|
| 7,750,209 B2* | 7/2010 | Tanaka et al. | | 800/298 |
| 7,884,066 B2* | 2/2011 | Ting | | 514/1.1 |
| 7,884,069 B2* | 2/2011 | Schaebitz et al. | | 424/85.1 |
| 7,884,263 B2* | 2/2011 | Dewey et al. | | 800/285 |
| 8,350,125 B2* | 1/2013 | Tanaka et al. | | 800/298 |
| 2008/0009032 A1 | 1/2008 | Tanaka et al. | | |

FOREIGN PATENT DOCUMENTS

| EP | 1 702 987 A1 | 9/2006 |
|---|---|---|
| WO | 2005/059141 | 6/2005 |

OTHER PUBLICATIONS

Database EMBL [Online] May 8, 2008, XP002602532 Database accession No. AB362991.
Database EMBL [Online] Oct. 2, 2003, XP002602533 Database accession No. AB042277.
Extended European Search Report for European Patent Application No. 08838174.4, dated Oct. 13, 2010.
Database GenBank [online] , Accession No. AB04227, <http://ww.ncbi.nlm.nih.gov/entrez/viewer.fcgi?37359709;OLD16:517464>, Oct. 2, 2003 uploaded [retrieved on Oct. 8, 2008], Nagashima S., et al., Definition: *Scutellaria baicalensis* UBGAT-I mRNA for UDP-glucuronate:baicalein 7-O-glucuronosyltransferase, complete cds.
Nagashima et al., "Purification and characterization of UDP-glucuronate: baicalein 7-O-glucuronosyltransferase from *Scutellaria baicalensis* Georgi. cell suspension cultures" *Phytochemistry* 53(5):533-538, 2000.
Ono et al., "Lamiales ni Okeru Flavonoid 7-i Haitotaika Koso no Kino Bunka", Proceedings of the Annual Meeting of the Japanese Society of Plant Physiologists, Mar. 15, 2008, vol. 49th, p. 137 (1pE04(141)), along with an English language translation.
Day et al., "Human metabolism of dietary flavonoids: identification of plasma metabolites of quercetin" *Free Radicals Research* 35:941-952, 2001.
Moon et al., "Identification of quercetin 3-O-β-D-glucuronide as an antioxidative metabolite in rat plasma after oral administration of quercetin" *Free Radical Biology & Medicine* 30(11): 1274-1285, 2001.
O'Leary et al., "Metabolism of quercetin-7- and quercetin-3-glucuronides by an in vitro hepatic model: the role of human β-glucuronidase, sulfotransferase, catechol-O-methyltransferase and multi-resistant protein 2 (MPR2) in flavonoid metabolism" *Biochemical Pharmacology* 65:479-491, 2003.
van der Woude et al., "Identification of 14 quercetin phase II mono- and mixed conjugates and their formation by rat and human phase II in vitro model systems" *Chem. Res. Toxicol.* 17:1520-1530, 2004.
Gao et al., "Free radical scavenging and antioxidant activities of flavonoids extracted from the radix of *Scutellaria baicalensis* Georgi" *Biochimica et Biophysica Acta* 1472:643-650, 1999.
Yamazaki et al., "Metabolomics and differential gene expression in anthocyanin chemo-varietal forms of *Perilla frutescens*" *Phytochemistry* 62:987-995, 2003.
International Search Report for PCT/JP2008/067613, mailed Oct. 21, 2008.
European Office Action issued with respect to European Patent Application No. 08 838 174.4, dated Aug. 25, 2011.
*Antirrhinum majus* AmUGTcg10 mRNA for UGT88D4, complete cds., DDBJ [online], Accession No. AB362988, [retrieved on Dec. 4, 2008], http://www.ncbi.nlm.nih.gov/entrez/viewer.fcgi?187761612:DDBJ:9066545, May 8, 2008.
*Sesamum indicum* SiUGT23 mRNA for UGT88D6, complete cds., DDBJ [online], Accession No. AB362990, [retrieved on Dec. 4, 208], ww.ncbi/nlm.nih.gov/entrez/viewer.
fcgi?187761616:DDBJ:9066547 , May 8, 2008.

(Continued)

*Primary Examiner* — Hope Robinson
(74) *Attorney, Agent, or Firm* — Greenblum & Bernstein, P.L.C.

(57) ABSTRACT

The present invention provides a novel UDP-glucuronosyltransferase and a polynucleotide encoding the same, for example, a polynucleotide comprising nucleotides 1 to 1359 of SEQ ID NO: 4, nucleotides 1 to 1365 of SEQ ID NO: 10, nucleotides 1 to 1371 of SEQ ID NO: 12, and nucleotides 1 to 1371 of SEQ ID NO: 22; or a polynucleotide encoding a protein having the amino acid sequence of SEQ ID NOS: 5, 11, 13 or 23. The invention provides a novel UDP-glucuronosyltransferase with a broad substrate specificity.

13 Claims, 8 Drawing Sheets

(56) References Cited

OTHER PUBLICATIONS

Ono E. et al., Yellow flowers generated by expression of the aurone biosynthetic pathway, proc. Natl. Acad.Sci.USA., vol. 103, No. 29, p. 11075-11080, full text, Jul. 18, 2006.

Asen, S. et al., Phytochemistry 11, 1972, pp. 2739-2741.

Shiono, M et al., Nature 436, 2005, pp. 791.

Search report from International Patent Application that issued with respect to patent family member International Patent Application No. PCT/JP2008/066365, mail date is Dec. 16, 2008.

* cited by examiner

Fig. 1

Formatted Alignments

```
AmUGTcg10aa   1   M E D T I V L Y A S A E H L N S M L L L G K L I N K H H P T I S V A I I S T A P N A A A S S V A D V   50
SlUGTaa       1   M E D T I V I Y T T P E H L N T M A V L A K F I S K H H P S V P I I L I S T A A E S A A A S I A A V   50
PfUGT50aa     1   M E G V I L L Y S S A E H L N S M L L L A T F I A K H H P S I P I T I L S S A D Y S A A A S V S T L   50
Sb7GATaa      1                         M A V L A K F I S K N H P S V P I I I I S N A P E S A A A S V A A I         34
                  M E D T I V L Y   S A E H L N S M . . L A K F I   K H H P S . P I . I I S . A     S A A A S V A .

AmUGTcg10aa  51   A A I S Y Q Q L K P A T L P S D L T K N P I E L F F E I P R L H N P N L L E A L E E L S L K S K V R  100
SlUGTaa      51   P S I T Y H R L P L P E I P P S L T K D R V E L F F E L P R L S N P N L R L A L Q E I S Q K A R I R  100
PfUGT50aa    51   P S I T Y R R L P P V A I P P D S I K N P V E A F F E I P R L Q N P N L R V A L E E I S Q K T R I R  100
Sb7GATaa     35   P S I S Y H R L P L P E I P P D M T T D R V E L F F E L P R L S N P N L L T A L Q Q I S Q K T R I R   84
                  P S I . Y . R L P     I P P D   T K     V E L F F E . P R L   N P N L       A L   E I S Q K . R I R

AmUGTcg10aa 101   A F V I D F F C N P A F E V S T S L N I P T Y F Y V S S G A F G L C G F L H F P T I D E T V E K D I  150
SlUGTaa     101   A F V I D F F C N A A F E V S T S L S I P T F Y Y F S S G S P T A T L V L H F Q T L D E T I P G D L  150
PfUGT50aa   101   A F V I D F F C N S A F E V S T S L S I P T Y Y V S T G S A G V C I F L Y F P T T D E T V A T D I    150
Sb7GATaa     85   A V I L D F F C N A A F E V P T S L N I P T Y Y Y F S A G T P T A I L T L Y F E T I D E T I P V D L  134
                  A F V I D F F C N   A F E V S T S L   I P T Y . Y   S . G .         L   F   T . D E T .     D .

AmUGTcg10aa 151   G E L N D I L E I P G C P P V L S S D F P K G M F F R K S N T Y K H F L D T A K N M R R A K G I V V  200
SlUGTaa     151   K D L D D F V E I P G L P P I Y S L D I P V A L L T R Q S L V Y Q S S V D I S K N L R K S A G F L V  200
PfUGT50aa   151   G D L R D F L E F P G S P I I H S S D L P Q L T F F R R S N V F K H M L D T S K N M Q K S S G I L T  200
Sb7GATaa    135   Q D L N D Y V D I P G L P P I H C L D I P V A L S P R K S L V Y K S S V D I S K N L R R S A G I L V  184
                    D L   D . . E I P G   P P I   S   D . P .         R . S   V Y K     . D   S K N   R . S   G I L V

AmUGTcg10aa 201   N A F D A M E F R A K E A L V N N L C V P N S P T P P V F L V G P L V G A S T T T K T T N E Q H E C  250
SlUGTaa     201   N G F D A L E F R A K E A I V N G L C V P N G P T P P V Y F I G P L V G D V D - A K A G G E E H E C  249
PfUGT50aa   201   N G F D A M E F R A K E A L T N G L C V P N G P T P P V Y L V G P L V A G S N - - - - A K K D H E C  246
Sb7GATaa    185   N G F D A L E F R A I G S H S Q R P M H F K G P T P P V Y F I G P L V G D V D - T K A G S E E H E C  233
                  N G F D A   E F R A K E A .   N   L C V P N G P T P P V Y . G P L V G       T T K A .     E . H E C

AmUGTcg10aa 251   L K W L D V Q P D R S V I F L C F G R R G L F S A D Q L K E I A I G L E N S G H R F L W S V R C P P  300
SlUGTaa     250   L R W L D T Q P S K S V I F L C F G R R G V F S A E Q L K E T A V A L E N S G H R F L W S V R N P P  299
PfUGT50aa   247   L L W L D R Q P S K S V V F L C F G R R G L F S G K Q L K E M A V A L E R S G Y R F L W S V R N P P  296
Sb7GATaa    234   L R W L D T Q P S K S V V F L C F G R R G L F S A K Q L K E T A A A L E N S G H R F L W S V R N P P  283
                  L . W L D   Q P S K S V . F L C F G R R G . F S A   Q L K E   A . A L E N S G H R F L W S V R N P P

AmUGTcg10aa 301   S K P N S Y N T D - P D L D E L L P E G F L S R T E T R G F V I K S W A P Q K E V L S H G A V G G F  349
SlUGTaa     300   E I M K N S - - D E P D L D E L L P E G F L E R T K D R G F V I K S W A P Q K E V L S H D S V G G F  347
PfUGT50aa   297   E N - R S P A E D - P D L D E L L P E G F L E R T K D I G F V V K S W A P Q K E V L S H D A V A G F  344
Sb7GATaa    284   E L K K A T G S D E P D L D E L L P E G F L E R T K D R G F V I K S W A P Q K E V L A H D S V G G F  333
                  E .                 D E P D L D E L L P E G F L E R T K D R G F V I K S W A P Q K E V L S H D   V G G F

AmUGTcg10aa 350   V T H C G R S S I L E A V S F G V P M I G W P I Y A E Q R M N R V F M V E E M K V A L Q L D E V E E  399
SlUGTaa     348   V T H C G R S S I S E G V W F G V P M I G W P V D A E Q K L N R T V L V E E M Q V A L P M E E A E G  397
PfUGT50aa   345   V T H C G R S S I L E A L V N G K P M I G W P M Y A E Q R M N K V F M V D E M K V A L P L E E E E D  394
Sb7GATaa    334   V T H C G R S S V S E G V W F G V P M I G W P V D A E L R L N R A V M V D D L Q V A L P L E E E A G  383
                  V T H C G R S S I     E . V     F G V P M I G W P .   A E Q R   N R .     M V . E M   V A L P L E E       E

AmUGTcg10aa 400   G F V A A V E L E K R V K E L M D S K N G R A V R Q R V K E M K V A A E V A V E K G G S S V V A L Q  449
SlUGTaa     398   G F V T A A E L E K R V R E L M E S K V G K A V R Q R V G E L K C S A R A A V T G N G S S L S D F K  447
PfUGT50aa   395   G F V T A V E L E K R L R Q L M E S K T G R D V R H R V A E M K A A A T A A M G E N G S A V V A L R  444
Sb7GATaa    384   G F V T A A E L E K R V R E L M E T K A G K A V R Q R V T E L K L S A R A A V A E N G S S L N D L K  433
                  G F V T A . E L E K R V R E L M E S K   G . A V R Q R V   E   K .   A   A A V   N G S S .         L .

AmUGTcg10aa 450   R F V D M V V S *   458
SlUGTaa     448   K F L L A T R D *   456
PfUGT50aa   445   K F I D S V T R D * 454
Sb7GATaa    434   K F L H A T R D     441
                  K F .       D
```

POLYNUCLEOTIDE ENCODING UDP-GLUCURONYL TRANSFERASE

This Application is the National Stage of International Application PCT/JP2008/067613, filed Sep. 29, 2008, which claims priority of Japanese Application No. 2007-267050, filed Oct. 12, 2007 and of Japanese Application No. 2008-067185, filed Mar. 17, 2008.

FIELD OF THE INVENTION

The present invention relates to a UDP-glucuronosyltransferase, a polynucleotide encoding the same, a vector containing the same, a transformant, and so on.

BACKGROUND OF THE INVENTION

Polyphenolic plant secondary metabolites including flavonoids and lignans with a rich dietary experience have attracted attention as functional materials over the years due to their functional properties represented by their antioxidative activities, and are already commercially available as health foods. For example, quercetin (flavonoid), OTPP (flavonoid), sesamin (lignan), etc. are representative materials for health foods.

The biosynthetic pathway of flavonoids in plant cells has been studied since old times. Biosynthetic enzymes that catalyze the metabolic pathway and genes encoding the enzymes are isolated, leading to a better understanding of their molecular mechanisms.

On the other hand, knowledge is insufficient on how the plant secondary metabolites would be metabolized to exhibit their functions, after their in vivo uptake.

It is known that glycosylation of plant secondary metabolites is generally catalyzed by an enzyme belonging to the superfamily called UDP-glycosyltransferase (UGT), irrespective of types of sugars (glucose, rhamnose, glucuronic acid, galactose, etc.). Further in the studies of sesamin, the secondary metabolites are shown to be present in vivo as glucuronides via catechol metabolites. It is thus considered that the glucuronides would play a part in developing the in vivo functions of plant secondary metabolites.

It is confirmed that four monoglucuronides are present as the metabolites of quercetin in mammals (Q-3-GlcA, Q-7-GlcA, Q-3'-GlcA and Q-4'-GlcA) (Literature 1: Day, A J et al. Free Radic. Res. 35, 941-952, 2001, Literature 2: Moon, J. H. et al. Free Radical Biology & Medicine 30, 1274-1285, 2001, Literature 3: O'Leary, K. A. et al. Biochemical Pharmacology 65, 479-491, 2003, and Literature 4: van der Woude, H. et al. Chem. Res. Toxicol. 17, 1520-1530, 2004); in order to understand these functions in vivo, it is necessary to obtain a sufficient amount of compounds to examine their activities. However, any appropriate UDP-glucuronosyltransferase showing a broad substrate specificity is unknown so far, and it was actually impossible to chemically synthesize a binding site-specific reaction product.

The radix of Labiatae *Scutellaria baicalensis* is called skullcap or "wogon" in Japanese, and it is known that 7-glucuronides of highly antioxidative flavones are accumulated therein. According to the borderline of pharmaceuticals to non-pharmaceuticals, the radix of *Scutellaria baicalensis* is classified into the pharmaceuticals (Literature 5: Gao, Z. et al. Biochimica et Biophysica Acta 1472, 643-650. 1999). To date, Sb7GAT is purified from Labiatae *Scutellaria baicalensis* as flavone 7-glucuronosyltransferase; this enzyme acts only on flavones with substituents such as hydroxyl group at the ortho position of the 7-OH flavones (baicalein, scutellarein, etc.) but does not act on apigenin and luteolin which are the major flavones and further not on quercetin which is one of flavonols (Literature 6: Nagashima S. et al., Phytochemistry 53, 533-538, 2000). A gene corresponding to this Sb7GAT is registered in GenBank (Accession No. AB042277) but its function remains unconfirmed.

On the other hand, it is known that flavone 7-glucuronides which are more diverse than skullcap or "wogon" are accumulated in *Perilla frutescens* a red-leaf variety with a dietary experience (Literature 7: Yamazaki, M. et al. Phytochemistry 62, 987-998. 2003).

LITERATURES

1. Day, A. J. et al., Free Radic. Res., 35, 941-952, 2001
2. Moon, J. H. et al., Free Radical Biology & Medicine, 30, 1274-1285, 2001
3. O'Leary, K. A. et al., Biochemical Pharmacology, 65, 479-491, 2003
4. van der Woude, H. et al., Chem. Res. Toxicol., 17, 1520-1530, 2004
5. Gao, Z. et al., Biochemica et Biophysica Acta, 1472, 643-650, 1999
6. Nagashima S. et al., Phytochemistry, 53, 533-538, 2000.
7. Yamazaki, M. et al., Phytochemistry, 62, 987-998, 2003

DISCLOSURE OF THE INVENTION

Problems To Be Solved by the Invention

Under these circumstances, it has been desired to identify a novel UDP-glucuronosyltransferase having a broader substrate specificity and a gene encoding the same.

Means of Solving the Problem

The present invention has been made in view of the foregoing circumstances and provides the following UDP-glucuronosyltransferases and polynucleotides encoding the same, as well as vectors bearing the same, transformants, and so on.

(1) A polynucleotide of any one of (a) through (f) below:

(a) a polynucleotide comprising a polynucleotide consisting of one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22;

(b) a polynucleotide comprising a polynucleotide encoding a protein having one amino acid sequence selected from the group consisting of SEQ ID NOs: 5, 11, 13 and 23;

(c) a polynucleotide comprising a polynucleotide encoding a protein consisting of an amino acid sequence with deletion, substitution, insertion and/or addition of 1 to 15 amino acids in one amino acid sequence selected from the group consisting of SEQ ID NOs: 5, 11, 13 and 23, and having a UDP-glucuronosyltransferase activity;

(d) a polynucleotide comprising a polynucleotide encoding a protein having an amino acid sequence having a homology of at least 80% to one amino acid sequence selected from the group consisting of SEQ ID NOs: 5, 11, 13 and 23 and having a UDP-glucuronosyltransferase activity;

(e) a polynucleotide comprising a polynucleotide encoding a protein that hybridizes under stringent conditions with a polynucleotide consisting of a nucleotide sequence complementary to one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22, and has a UDP-glucuronosyltransferase activity; and, (f) a polynucleotide comprising a polynucleotide encoding a protein that hybridizes under stringent conditions with a polynucleotide consisting of a nucleotide sequence complementary to the nucleotide sequence of a polynucleotide encoding a protein consisting of one amino acid sequence selected from the group consisting of SEQ ID NOs: 5, 11, 13 and 23, and has a UDP-glucuronosyltransferase activity.

(2) The polynucleotide according to (1) above, which is any one of (g) through (j) below:

(g) a polynucleotide comprising a polynucleotide encoding a protein consisting of an amino acid sequence with deletion, substitution, insertion and/or addition of not greater than 10 amino acids (i.e. 0-10 amino acids) in one amino acid sequence selected from the group consisting of SEQ ID NOs: 5, 11, 13 and 23, and having a UDP-glucuronosyltransferase activity;

(h) a polynucleotide comprising a polynucleotide encoding a protein having an amino acid sequence having a homology of at least 90% to one amino acid sequence selected from the group consisting of SEQ ID NOs: 5, 11, 13 and 23, and having a UDP-glucuronosyltransferase activity;

(i) a polynucleotide comprising a polynucleotide encoding a protein that hybridizes under high stringent conditions with a polynucleotide consisting of a nucleotide sequence complementary to one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22, and has a UDP-glucuronosyltransferase activity; and, (j) a polynucleotide comprising a polynucleotide encoding a protein that hybridizes under high stringent conditions with a polynucleotide consisting of a nucleotide sequence complementary to the nucleotide sequence of a polynucleotide encoding a protein consisting of one amino acid sequence selected from the group consisting of SEQ ID NOs: 5, 11, 13 and 23, and has a UDP-glucuronosyltransferase activity.

(3) The polynucleotide according to (1) above, which comprises a polynucleotide consisting of the nucleotide sequence at positions 1 to 1359 in the nucleotide sequence represented by SEQ ID NO: 4.

(4) The polynucleotide according to (1) above, which comprises a polynucleotide consisting of the nucleotide sequence at positions 1 to 1365 in the nucleotide sequence represented by SEQ ID NO: 10.

(5) The polynucleotide according to (1) above, which comprises a polynucleotide consisting of the nucleotide sequence at positions 1 to 1371 in the nucleotide sequence represented by SEQ ID NO: 12.

(6) The polynucleotide according to (1) above, which comprises a polynucleotide consisting of the nucleotide sequence at positions 1 to 1371 in the nucleotide sequence represented by SEQ ID NO: 22.

(7) The polynucleotide according to (1) above, which comprises a polynucleotide encoding the protein consisting of the amino acid sequence represented by SEQ ID NO: 5.

(8) The polynucleotide according to (1) above, which comprises a polynucleotide encoding the protein consisting of the amino acid sequence represented by SEQ ID NO: 11.

(9) The polynucleotide according to (1) above, which comprises a polynucleotide encoding the protein consisting of the amino acid sequence represented by SEQ ID NO: 13.

(10) The polynucleotide according to (1) above, which comprises a polynucleotide encoding the protein consisting of the amino acid sequence represented by SEQ ID NO: 23.

(11) The polynucleotide according to any one of (1) to (10) above, which is a DNA.

(12) A protein encoded by the polynucleotide according to any one of (1) to (11) above.

(13) A vector comprising the polynucleotide according to any one of (1) to (11) above.

(14) A transformant, wherein the polynucleotide according to any one of (1) to (11) above is introduced.

(15) A transformant, wherein the vector according to (13) above is introduced.

(16) A method for producing the protein of claim 12, which comprises using the transformant according to (14) or (15) above.

(17) A method for producing a glucuronide, which comprises forming the glucuronide from UDP-glucuronic acid and a flavonoid using the protein according to (12) above as a catalyst.

Advantageous Effect of the Invention

The polynucleotide of the present invention is useful for the production of a novel UDP-glucuronosyltransferase by introducing the polynucleotide into, e.g., a transformant. In a preferred embodiment of the invention, the UDP-glucuronosyltransferase has a broad substrate specificity and an activity of glucuronidation of diverse glycosyl acceptor substrates.

BRIEF DESCRIPTION OF DRAWINGS

FIG. 1 shows alignments of the amino acid sequences of AmUGTcg10 (SEQ ID NO: 13) derived from *Antirrhinum majus*, S1UGT (SEQ ID NO: 11) derived from *Scutellaria laeteviolacea* v. *yakusimensis*, PfUGT50 (SEQ ID NO: 5) derived from *Perilla frutescens* a red-leaf variety and Sb7GAT (SEQ ID NO: 26) derived from *Scutellaria baicalensis*.

SEQUENCE LISTING FREE TEXT

Figure 2:
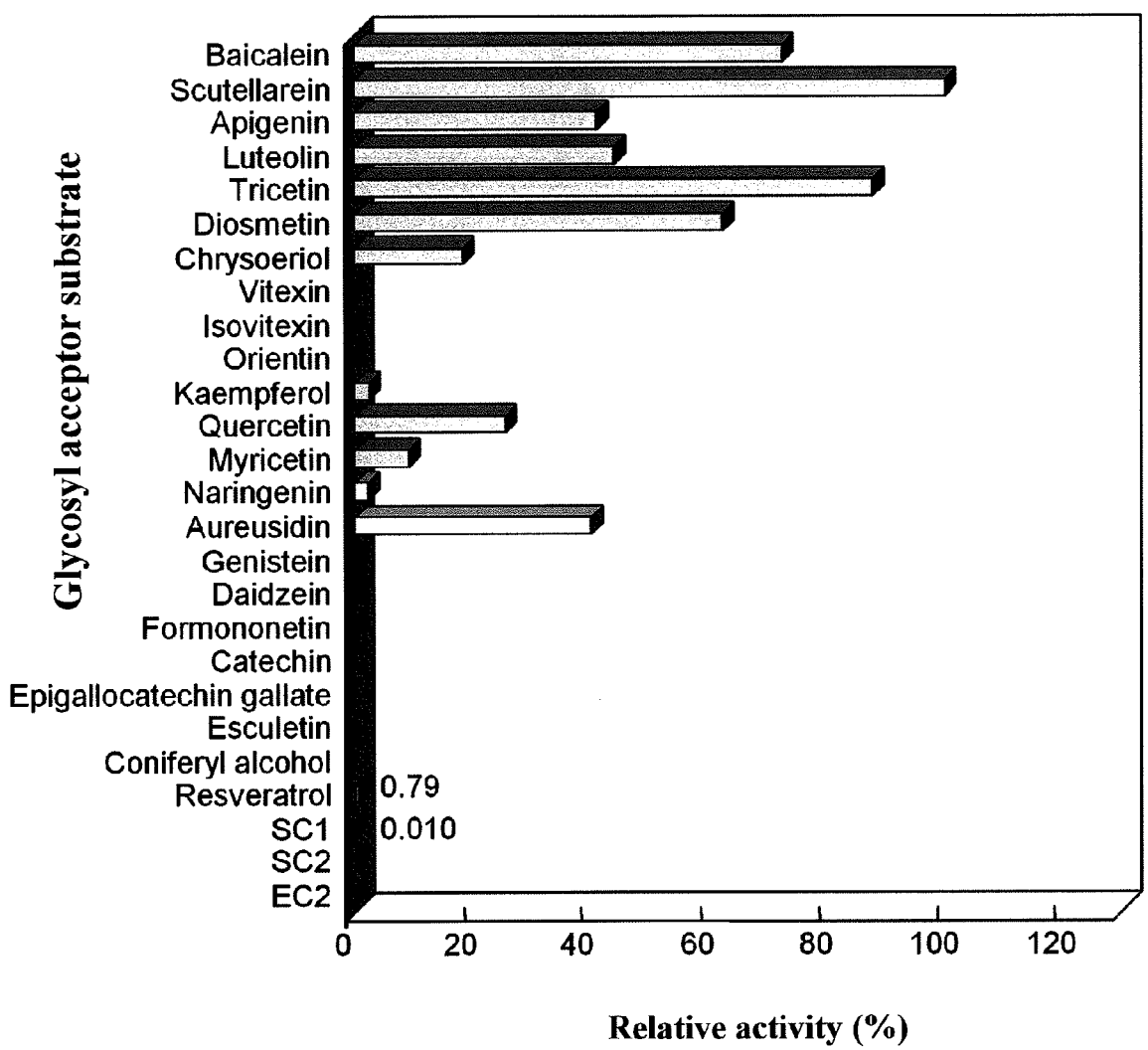
FIG. 2 shows the results of analysis on the specificity of glycosyl acceptor substrates for PfUGT50.

SEQ ID NO: 1 synthetic DNA
SEQ ID NO: 2 synthetic DNA
SEQ ID NO: 6 synthetic DNA
SEQ ID NO: 7 synthetic DNA
SEQ ID NO: 8 synthetic DNA
SEQ ID NO: 9 synthetic DNA
SEQ ID NO: 14 synthetic DNA
SEQ ID NO: 15 synthetic DNA
SEQ ID NO: 16 synthetic DNA
SEQ ID NO: 17 synthetic DNA
SEQ ID NO: 18 synthetic DNA
SEQ ID NO: 19 synthetic DNA
SEQ ID NO: 20 synthetic DNA
SEQ ID NO: 21 synthetic DNA
SEQ ID NO: 24 synthetic DNA
SEQ ID NO: 25 synthetic DNA

BEST MODE FOR CARRYING OUT THE INVENTION

Hereinafter, the UDP-glucuronosyltransferases of the invention, the polynucleotide encoding the same, the vector bearing the same, the transformant and so on are described in detail.

1. Polynucleotide of the Invention

First, the present invention provides (a) a polynucleotide (specifically a DNA, hereinafter sometimes merely referred to as "DNA") comprising a polynucleotide consisting of one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22; and (b) a polynucleotide comprising a polynucleotide encoding a protein having one amino acid sequence selected from the group consisting of SEQ ID NOS: 5, 11, 13 and 23. The DNA targeted in the present invention is not limited only to the DNA encoding UDP-glucuronosyltransferase described above but also includes other DNAs encoding a protein functionally equivalent to this protein. The functionally equivalent protein is, for example, (c) a protein consisting of an amino acid sequence with deletion, substitution, insertion and/or addition of 1 to 15 amino acids in one amino acid sequence selected from the group consisting of SEQ ID NOs: 5, 11, 13 and 23, and having a UDP-glucuronosyltransferase activity. Such a protein includes a protein consisting of one amino acid sequence selected from the group consisting of SEQ ID NOs: 5, 11, 13 and 23 wherein 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 or 1 amino acid(s) is/are deleted, substituted, inserted and/or added and having the UDP-glucuronosyltransferase activity. In general, the number of deletions, substitutions, insertions, and/or additions is preferably smaller. Such proteins include a protein having an amino acid sequence having a homology of approximately 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to one amino acid sequence selected from the group consisting of SEQ ID NOs: 5, 11, 13 and 23, and having the UDP-glucuronosyltransferase activity. As the homology percentage described above is higher, the protein is preferred in general.

As used herein, the term "UDP-glucuronosyltransferase activity" refers to an activity of catalyzing the reaction that involves the glucuronidation of hydroxyl groups in flavonoids, stilbenes, lignans, etc. (glucuronidation of, e.g., a flavone at the position 7-OH) to form glucuronides.

The UDP-glucuronosyltransferase activity can be assayed by reacting, for example, UDP-glucuronic acid with a glycosyl acceptor substrate (e.g., a flavone) in the presence of an enzyme to be assayed and analyzing the reaction product by HPLC (cf., EXAMPLES described below for more details).

The present invention further includes (e) a polynucleotide comprising a polynucleotide encoding a protein that hybridizes under stringent conditions with a polynucleotide consisting of a nucleotide sequence complementary to one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22, and has the UDP-glucuronosyltransferase activity; and (f) a polynucleotide comprising a polynucleotide encoding a protein that hybridizes under stringent conditions with a polynucleotide consisting of a nucleotide sequence complementary to the nucleotide sequence of a polynucleotide encoding a protein consisting of one amino acid sequence selected from the group consisting of SEQ ID NOs: 5, 11, 13 and 23, and has the UDP-glucuronosyltransferase activity.

As used herein, the "polynucleotide" refers to a DNA or RNA.

As used herein, the term "polynucleotide that hybridizes under stringent conditions" refers to, for example, a polynucleotide obtained by colony hybridization, plaque hybridization, Southern hybridization or the like, using as a probe all or part of a polynucleotide consisting of a nucleotide sequence complementary to one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12, and the nucleotide sequence at positions 1 to 1371 in the nucleotide sequence represented by SEQ ID NO: 22 or a polynucleotide consisting of a nucleotide sequence complementary to the nucleotide sequence of a polynucleotide encoding one amino acid sequence selected from the group consisting of SEQ ID NOs: 5, 11, 13 and 23. The hybridization method may be a method described in, for example, Sambrook & Russell, Molecular Cloning: A Laboratory Manual Vol. 3, Cold Spring Harbor, Laboratory Press 2001, Ausubel, Current Protocols in Molecular Biology, John Wiley & Sons 1987-1997, etc.

As used herein, the "stringent conditions" may be any of low-stringent conditions, medium-stringent conditions or high-stringent conditions. The "low-stringent conditions" are, for example, 5×SSC, 5×Denhardt's solution, 0.5% SDS, 50% formamide and 32° C. The "medium-stringent conditions" are, for example, 5×SSC, 5×Denhardt's solution, 0.5% SDS, 50% formamide and 42° C. The "high-stringent conditions" are, for example, 5×SSC, 5×Denhardt's solution, 0.5% SDS, 50% formamide and 50° C. Under these conditions, as the temperature is higher, a DNA with higher homology is expected to be obtained efficiently at higher temperature, although multiple factors are involved in the hybridization stringency including temperature, probe concentration, probe length, ionic strength, time, salt concentration and the like. Those skilled in the art may realize similar stringency by appropriately selecting these factors.

When a commercially available kit is used for hybridization, for example, Alkphos Direct Labeling Reagents (manufactured by Amersham Pharmacia) can be used. In this case, according to the attached protocol, a membrane is incubated with a labeled probe overnight, the membrane is washed with a primary wash buffer containing 0.1% (w/v) SDS at 55° C. and the hybridized DNA can then be detected.

Other polynucleotides that can be hybridized include DNAs having a homology of approximately 60% or higher, approximately 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher. 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher, to a DNA encoding one nucleotide sequence selected from the group consisting of the nucleotide sequence at positions 1 to 1359 in the nucleotide sequence represented by SEQ ID NO: 4, the nucleotide sequence at positions 1 to 1365 in the nucleotide sequence represented by SEQ ID NO: 10, the nucleotide sequence at positions 1 to 1371 in the nucleotide sequence represented by SEQ ID NO: 12 and the nucleotide sequence at positions 1 to 1371 in the nucleotide sequence represented by SEQ ID NO: 22, or one amino acid sequence selected from the group consisting of SEQ ID NOs: 5, 11, 13 and 23, as calculated by homology search software, such as FASTA and BLAST using default parameters.

Homology between amino acid sequences or nucleotide sequences can be determined by using algorithm BLAST by Karlin and Altschul (Proc. Natl. Acad. Sci. USA, 87: 2264-2268, 1990; Proc. Natl. Acad. Sci. USA, 90: 5873, 1993). Programs called BLASTN and BLASTX based on BLAST algorithm have been developed (Altschul, S. F. et al., J. Mol. Biol., 215: 403, 1990). When a nucleotide sequence is sequenced using BLASTN, the parameters are, for example, score=100 and word length=12. When an amino acid sequence is sequenced using BLASTX, the parameters are, for example, score=50 and word length=3. When BLAST and Gapped BLAST programs are used, default parameters for each of the programs are employed.

The polynucleotide of the invention described above can be acquired by known genetic engineering means or known synthetic means.

2. Protein of the Invention

In a further embodiment, the present invention also provides the protein encoded by any one of the polynucleotides (a) through (f) described above. The protein of the invention which is preferred is a protein consisting of an amino acid sequence with deletion, substitution, insertion and/or addition of 1 to 15 amino acids in one amino acid sequence selected from the group consisting of SEQ ID NOs: 5, 11, 13 and 23, and having a UDP-glucuronosyltransferase activity. Such a protein includes a protein consisting of an amino acid sequence wherein amino acid residues with the number described above are deleted, substituted, inserted and/or added in one amino acid sequence selected from the group consisting of SEQ ID NOs: 5, 11, 13 and 23 and having the UDP-glucuronosyltransferase activity. The protein also includes a protein having the amino acid sequence having the homology described above to one amino acid sequence selected from the group consisting of SEQ ID NOs: 5, 11, 13 and 23 and having the UDP-glucuronosyltransferase activity. These proteins may be obtained by using site-directed mutagenesis described in Sambrook & Russell, Molecular Cloning: A Laboratory Manual, Vol. 3, Cold Spring Harbor, Laboratory Press 2001, Ausubel, Current Protocols in Molecular Biology, John Wiley & Sons 1987-1997, Nuc. Acids Res., 10, 6487 (1982), Proc. Natl. Acad. Sci. USA, 79, 6409 (1982), Gene, 34, 315 (1985), Nuc. Acids Res., 13, 4431 (1985), Proc. Natl. Acad. Sci. USA, 82, 488 (1985), etc.

The deletion, substitution, insertion and/or addition of one or more amino acid residues in an amino acid sequence of the protein of the invention means that one or a plurality of amino acid residues are deleted, substituted, inserted and/or added at one or a plurality of positions in the same amino acid sequence. Two or more types of deletion, substitution, insertion and addition may occur concurrently.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method) and the tBoc method (t-butyloxycarbonyl method). In addition, peptide synthesizers available from Advanced ChemTech, Perkin Elmer, Pharmacia, Protein Technology Instrument, Synthecell-Vega, Per-Septive, Shimadzu Corp., etc. may also be used for the chemical synthesis.

Herein, the protein of the invention is a UDP-glucuronosyltransferase. The term "UDP-glucuronosyltransferase" catalyzes the reaction of transferring the glucuronyl group from UDP-glucuronic acid as a glycosyl donor onto a glycosyl acceptor substrate to form the glucuronide and UDP. In the present invention, the glycosyl acceptor substrate is, for example, a flavonoid, a stilbene and a lignan.

The flavonoid includes flavones, flavonols, flavanones, isoflavones, flavone C-glycosides, aurones, catechins, and the like. Among them, examples of the flavones include baicalein, scutellarein, apigenin, luteolin, tricetin, diosmetin, chrysoeriol, etc. Examples of the flavonols include quercetin, myricetin, kaempferol, etc. An example of the flavanones is naringenin. Examples of the isoflavones are genistein, daidzein and formononetin. Examples of the flavone C-glycosides include vitexin, isovitexin and orientin. An example of the aurones is aureusidin. Examples of the catechins are catechin and epigallocatechin gallate.

The stilbene includes resveratrol and its glycoside piceid, etc.

The lignan includes (+)-pinoresinol, (+)-piperitol, (+)-sesaminol, (+)-secoisolariciresinol, (+)-sesamin catechol 1) (SC1), (+)-sesamin catechol 2 (SC2), (+)-episesamin catechol 2 (EC2), matairesinol, etc.

For example, the UDP-glucuronosyltransferase having the amino acid sequence of SEQ ID NO: 5 (PfUGT50) shows the activity when the glycosyl acceptor substrate is a flavonoid such as baicalein, apigenin, scutellarein, luteolin, tricetin, diosmetin, chrysoeriol, quercetin, myricetin, kaempferol, naringenin, aureusidin, etc., a stilbene such as resveratrol, etc., a lignan such as SC1, etc., and shows a potent activity as compared to other glycosyl acceptor substrates, especially when the glycosyl acceptor substrate is baicalein, apigenin, scutellarein, luteolin, tricetin, diosmetin, chrysoeriol, quercetin and aureusidin.

The UDP-glucuronosyltransferase having the amino acid sequence of SEQ ID NO: 11 (S1UGT) shows the activity when the glycosyl acceptor substrate is a flavonoid such as baicalein, apigenin, scutellarein, luteolin, tricetin, diosmetin, chrysoeriol, quercetin, kaempferol, naringenin, genistein, daidzein, formononetin, myricetin, etc., a coumarine such as esculetin, etc., a stilbene such as resveratrol, etc., a lignan such as SC1, SC2, EC2, etc., and shows a potent activity as compared to other glycosyl acceptor substrates, especially when the glycosyl acceptor substrate is baicalein and apigenin.

The UDP-glucuronosyltransferase having the amino acid sequence of SEQ ID NO: 13 (AmUGTcg10) shows the activity when the glycosyl acceptor substrate is a flavonoid such as baicalein, apigenin, scutellarein, luteolin, tricetin, diosmetin, chrysoeriol, quercetin, kaempferol, naringenin, aureusidin, etc., a stilbene such as resveratrol, etc., and shows a potent activity as compared to other glycosyl acceptor substrates, especially when the glycosyl acceptor substrate is a flavonoid such as baicalein, apigenin, scutellarein, luteolin, tricetin, diosmetin, chrysoeriol, kaempferol, naringenin, etc.

The UDP-glucuronosyltransferase having the amino acid sequence of SEQ ID NO: 23 (SiUGT23) shows the activity when the glycosyl acceptor substrate is a flavonoid such as baicalein, apigenin, scutellarein, luteolin, tricetin, diosmetin, chrysoeriol, isovitexin, quercetin, kaempferol, naringenin, aureusidin, formononetin, etc., a coumarine such as esculetin, etc., a stilbene such as resveratrol, etc., and shows a potent activity as compared to other glycosyl acceptor substrates, especially when the glycosyl acceptor substrate is a flavonoid such as baicalein, scutellarein, luteolin, tricetin, kaempferol, aureusidin, etc.

3. Vector and Transformant Bearing the Same

In another embodiment, the present invention provides the expression vector comprising the polynucleotide of the present invention. The vector of the invention comprises any one of (a) through (f) described above. Preferably, the expression vector of the invention comprises any one of the polynucleotides (g) through (j). More preferably, the expression vector of the invention comprises a polynucleotide comprising one polynucleotide selected from the group consisting of a polynucleotide consisting of the nucleotide sequence at positions 1 to 1359 in the nucleotide sequence represented by SEQ ID NO: 4, a polynucleotide consisting of the nucleotide sequence at positions 1 to 1365 in the nucleotide sequence represented by SEQ ID NO: 10, a polynucleotide consisting of the nucleotide sequence at positions 1 to 1371 in the nucleotide sequence represented by SEQ ID NO: 12 and a polynucleotide consisting of the nucleotide sequence at positions 1 to 1371 in the nucleotide sequence represented by SEQ ID NO: 22, or one polynucleotide selected from the group consisting of a polynucleotide encoding a protein consisting of the amino acid sequence of SEQ ID NO: 5, a polynucleotide encoding a protein consisting of the amino acid sequence of SEQ ID NO: 11, a polynucleotide encoding a protein consisting of the amino acid sequence of SEQ ID NO: 13 and a polynucleotide encoding a protein consisting of the amino acid sequence of SEQ ID NO: 23.

The vector of the invention is generally constructed to contain an expression cassette comprising (i) a promoter that can be transcribed in a host cell, (ii) any of the polynucleotides described in (a) to (j) above that is linked to the promoter, and (iii) a signal that functions in the host cell with respect to the transcription termination and polyadenylation of RNA molecule. The vector thus constructed is introduced into a host cell. To construct the expression vector, methods using a plasmid, phage or cosmid are used but are not particularly limited.

Specific types of the vector are not particularly limited, and vectors capable of expressing in a host cell can be suitably selected. That is, a suitable promoter sequence may be chosen depending upon the type of the host cell to reliably express the polynucleotide of the invention, and a vector obtained by incorporating this sequence and the polynucleotide of the present invention into various plasmids or the like may be used as an expression vector.

The expression vector of the present invention contains an expression control region (for example, a promoter, a terminator, and/or a replication origin, etc.) depending on the type of a host to be introduced. A conventional promoter (for example, trc promoter, tac promoter, lac promoter, etc.) is used as a promoter for a bacterial expression vector. As a promoter for yeast, there are used, for example, a glyceraldehyde 3-phosphate dehydrogenase promoter, PH05 promoter, etc. As a promoter for fungi there are used, for example, amylase, trpC, etc. Additionally, a viral promoter (e.g., SV40 early promoter, SV40 late promoter, etc.) is used as a promoter for animal-derived host cell.

The expression vector preferably contains at least one selective marker. The marker available includes an auxotrophic marker (ura5, niaD), a drug-resistant marker (hygromycin, zeocin), a geneticin-resistant marker (G418r), a copper-resistant gene (CUP1) (Marin et al., Proc. Natl. Acad. Sci. USA, 81, 337, 1984), a cerulenin resistant gene (fas2m, PDR4) (Junji Inokoshi et al., Biochemistry, 64, 660, 1992; and Hussain et al., Gene, 101: 149, 1991), and the like.

The present invention provides the transformant in which the polynucleotide described in any of (a) to (j) above is introduced.

A method of preparing (method of producing) the transformant is not particularly limited and includes, for example, a method which comprises introducing the recombinant vector into a host followed by transformation. The host cell used herein is not particularly limited and various known cells may be preferably used. Specific examples are bacteria such as *Escherichia coli*, etc., yeast (budding yeast *Saccharomyces cerevisiae*, fission yeast *Schizosaccharomyces pombe*), nematode (*Caenorhabditis elegans*), oocyte of African clawed frog (*Xenopus laevis*), etc. Culture media and conditions suitable for the host cells above are well known in the art. The organism to be transformed is not particularly limited, and includes various microorganisms, plants and animals given as examples of the host cells above.

For transformation of the host cell, there may be used generally known methods. For example, methods that can be used include but not limited to the electroporation method (Mackenzie D. A. et al., Appl. Environ. Microbiol., 66, 4655-4661, 2000), the particle delivery method (method described in JPA 2005-287403 "Method of Breeding Lipid-Producing Fungus"), the spheroplast method (Proc. Natl. Acad. Sci. USA, 75: 1929 (1978)), the lithium acetate method (J. Bacteriology, 153: 163 (1983)), and methods described in Proc. Natl. Acad. Sci. USA, 75: 1929 (1978), Methods in yeast genetics, 2000 Edition: A Cold Spring Harbor Laboratory Course Manual, etc.

4. Method of Producing the Protein of the Invention

In yet another embodiment, the present invention provides a method of producing the protein of the present invention using the transformants described above.

Specifically, the protein of the invention may be obtained by isolating and purifying the protein of the invention from the culture of the transformant described above. As used herein, the culture refers to any one of a culture broth, cultured bacteria or cultured cells, and the homogenate of cultured bacteria or cultured cells. Conventional methods may be used to isolate and purify the protein of the invention.

Specifically, when the protein of the invention accumulates within cultured bacteria or within cultured cells, a crude extract of the protein of the invention may be obtained by culturing the bacteria or cells, then disrupting the bacterial or cells using a conventional technique (e.g., ultrasonication, lysozymes, freezing and thawing, etc.) and applying a conventional method such as centrifugation or filtration. When the protein of the invention is accumulated in the culture broth, the culture supernatant containing the protein of the invention can be obtained, after completion of the incubation, by separating the bacteria or cells from the culture supernatant in a conventional manner (e.g., centrifugation, filtration, etc.).

Purification of the protein of the invention contained in the extract or culture supernatant obtained as described above can be performed by a conventional method of separation and purification. The separation and purification methods including ammonium sulfate precipitation, gel filtration chromatography, ion exchange chromatography, affinity chromatography, reversed phase high performance liquid chromatography, dialysis, and ultrafiltration, etc. may be used singly or in a suitable combination.

5. Method of Producing the Glucuronide

The present invention further provides a method of producing the glucuronide using the protein of the present invention. The protein of the invention catalyzes the reaction of transferring the glucuronic acid from UDP-glucuronic acid to a glycosyl acceptor substrate (e.g., a flavonoid, a stilbene or a lignan) and therefore, the glucuronide can be produced from the glycosyl acceptor substrate and UDP-glucuronic acid by using the protein of the invention. The glycosyl acceptor substrate is preferably a flavonoid.

The glucuronide can be produced, for example, by preparing a solution containing 1 mM glycosyl acceptor substrate, 2 mM UDP-glucuronic acid, 50 mM calcium phosphate buffer (pH 7.5) and 20 µM of the protein of the invention is prepared and reacting them at 30° C. for 30 minutes. The glucuronide can be isolated/purified from this solution by known methods. Specifically, e.g., ammonium sulfate precipitation, gel filtration chromatography, ion exchange chromatography, affinity chromatography, reversed phase high performance liquid chromatography, dialysis, ultrafiltration, etc. can be used alone or in an appropriate combination.

The glucuronide thus obtained is useful as a reagent for inspecting the in vivo functions, an antioxidant, etc. (Gao, Z., Huang, K., Yang, X., and Xu, H. (1999) Biochimica et Biophysica Acta, 1472, 643-650).

The present invention is described in more details with reference to EXAMPLES below but is not deemed to be limited thereto.

EXAMPLE 1

1. Outline of Example 1

In this EXAMPLE, Sb7GAT homologue gene (S1UGT) was cloned from *Scutellaria laeteviolacea* v. *yakusimensis* by PCR and using this gene as a probe, it was attempted to isolate 7-glucuronosyltransferase of the flavonoid from the cDNA library of *Perilla frutescens* a red-leaf variety, which accumulates the 7-glucuronide of flavonoid.

As a result of screening, PfUGT50 having an activity to transfer the glucuronic acid to the 7-hydroxy group of a flavone was identified in glycosyltransferase PfUGT derived from *Perilla frutescens* a red-leaf variety. This PfUGT50 had the glucuronosyl transfer activity not only to flavones such as baicalein, scutellarein, apigenin, luteolin, etc. but also to quercetin which is a flavonol. Accordingly, the use of PfUGT50 enables to glucuronidate the 7-position of various flavonoids including flavones in vivo.

Also, S1UGT derived from *Scutellaria laeteviolacea* v. *yakusimensis*, which was isolated as a screening probe, showed the glucuronosyl transfer activity to various flavonoids. Scrophulariaceae *Antirrhinum majus* was also searched for UGT (UDP-glucuronosyltransferase) highly homologous to PfUGT50 and S1UGT to identify AmUGTcg10 as UGT from *Antirrhinum majus*. The AmUGTcg10 protein expressed in *Escherichia coli*, which is UGT derived from *Antirrhinum majus*, showed the glucuronosyl transfer activity to apigenin, quercetin and naringenin. It was therefore shown that PfUGT50 from *Perilla frutescens* a red-leaf variety, S1UGT from *Scutellaria laeteviolacea* v. *yakusimensis* and AmUGTcg10 from *Antirrhinum majus* described above had the activity to transfer the 7-glucuronic acid of flavonoids.

2. Isolation of Glucosyltransferase Gene from the *Perilla Frutescens* cDNA Library (1) Preparation of Probe The molecular biological method used in this EXAMPLE was in accordance with the method described in Molecular Cloning (Sambrook et al, Cold Spring Harbour Laboratory Press, 2001), unless otherwise indicated in detail.

After total RNA was extracted from the radix of *Scutellaria laeteviolacea* v. *yakusimensis* using RNeasy Plant Mini Kit (QIAGEN), SuperScript™ First-Strand Synthesis System for RT-PCR (Invitrogen Corp.) was used under the conditions recommended by the manufacturer to synthesize cDNA from 1 µg of total RNA. Based on the sequence of Sb7GAT from *Scutellaria baicalensis* (GenBank accession No. AB042277), primer-Fw (SEQ ID NO: 1) and primer-Rv (SEQ ID NO: 2) were designed. Using the primers, PCR was performed using as a template cDNA from *Scutellaria laeteviolacea* v. *yakusimensis*.

```
SEQ ID NO: 1:
S1UGT-Fw: 5'-AAACATATGGCGGTGCTGGCGAAGTTC-3'

(the underlined is the NdeI site)

SEQ ID NO: 2:
S1UGT-Rv: 5'-TTTTGATCATTAATCCCGAGTGGCGTGAAG-3'

(the underlined is the BclI site)
```

Specifically, the PCR solution (50 µl) was composed of 1 µl of cDNA (*Scutellaria laeteviolacea* v. *yakusimensis*), 1× Taq buffer (TaKaRa), 0.2 mM dNTPs, 0.4 pmol each/µl of the primers (SEQ ID NOs: 1 and 2) and 2.5 U of rTaq polymerase. PCR was performed by reacting at 94° C. for 3 minutes and then amplified for 30 cycles with each cycle consisting of reacting at 94° C. for a minute, 53° C. for a minute and 72° C. for 2 minutes.

The amplified fragment was inserted into the multicloning site of pCR-TOPOII vector (Invitrogen), and the nucleotide sequence of the inserted fragment was determined by the primer walking method using synthetic oligonucleotide primer with DNA Sequencer Model 3100 (Applied Biosystems). As a result of the analysis on the nucleotide sequence obtained by CLUSTAL-W Program (MACVECTOR 7.2.2 software, Accerly Corporation), it was confirmed that the partial sequence of UGT from *Scutellaria laeteviolacea* v. *yakusimensis* highly homologous to *Scutellaria baicalensis* was obtained (SEQ ID NO: 3). This UGT from *Scutellaria laeteviolacea* v. *yakusimensis* was used as a template for the screening probe in the form of S1UGT partial sequence.

The fragment obtained by RT-PCR was labeled by using the Non-Radioisotope DIG-Nucleic Acid Detection System (Roche Diagnostics) in accordance with the conditions recommended by the manufacturer. Specifically, the PCR solution (50 µl) was composed of 1 µl of each cDNA, 1× Taq buffer (TaKaRa), 0.2 mM dNTPs, 0.4 pmol each/µl of the primers (SEQ ID NOs: 1 and 2) and 2.5 U of rTaq polymerase. PCR was performed by reacting at 94° C. for 5 minutes and then amplified for 30 cycles with each cycle consisting of reacting at 94° C. for a minute, 53° C. for a minute and 72° C. for 2 minutes. After the S1UGT fragment was confirmed to be labeled by agarose electrophoresis, this DIG-labeled fragment was used for the following experiment as a probe for hybridization.

(2) Hybridization

Using the S1UGT probe described above, the cDNA library derived from *Perilla frutescens* (species: aka-chirimen-jiso or red-leaved perilla) (Yonekura-Sakakibara, K. et al., Plant Cell Physiol. 41, 495-502. 2000) was screened by using the Non-Radioisotope DIG-Nucleic Acid Detection System (Roche Diagnostics) in accordance with the conditions recommended by the manufacturer.

A hybridization buffer (5×SSC, 30% formamide, 50 mM sodium phosphate buffer (pH 7.0), 1% SDS, 2% blocking reagent (Roche), 0.1% lauroylsarcosine and 80 g/ml salmon sperm DNA) was used for prehybridization at 40° C. for an hour, and the denatured probe was then added, followed by incubation overnight. The membrane was rinsed in 4×SSC wash buffer containing 1% SDS at 58° C. for 30 minutes. Approximately 1×10$^6$ pfu plaques were screened to obtain 300 positive clones.

(3) Gene Identification

The positive clones were purified to a single plaque by secondary screening. Using a primer pair of M13RV and M13M4 (−20), the inserted fragment was amplified to determine the DNA sequence of the inserted part. Using the putative amino acid sequence deduced based on the determined DNA sequence, database search was performed by Blast x to obtain perilla UGT (PfUGT50) having high homology to S1UGT and Sb7GAT (SEQ ID NOs: 4 and 5).

The results of analysis on the obtained full-length PfUGT50, S1UGT and Sb7GAT on the CLUSTAL-W program (MACVECTOR 7.2.2 software, Accerly Corporation) strongly suggested that both S1UGT and Sb7GAT were incomplete ORF (open reading frame) missing the 3'- and 5'-regions. So, rapid amplification of cDNA end (hereinafter RACE) was conducted using a Gene Racer Kit (Invitrogen), according to the protocol recommended by the manufacturer to amplify the 5'- and 3'-regions of S1UGT. For RACE, the following primer sets specific to each S1UGT gene were used (SEQ ID NOs: 6 to 9).

```
SEQ ID NO: 6: GR-S1UGT-Rv:
5'-TGG GAG GCA AAC CAG GGA TCT CGA CAA

SEQ ID NO: 7: S1UGT-nest-Rv:
5'-AAT CAT CCA AAT CTT TAA GGT

SEQ ID NO: 8: GR-S1UGT-Fw:
5'-AGA AGG GGT GTG TTC TCC GCT GAG CAA

SEQ ID NO: 9: S1UGT-nest-Fw:
5'-GAA CAG CGG TCA CAG ATT TCT
```

The nucleotide sequences of the respective amplified products were determined by the primer walking method using synthetic oligonucleotide primers to obtain the S1UGT gene including the full-length ORF and the amino acid sequence (SEQ ID NOs: 10 and 11).

In addition to *Perilla frutescens* and *Scutellaria laeteviolacea* v. *yakusimensis*, 7-glucuronides of apigenin, which is one of flavones, are reported also on Scrophulariaceae, *Antirrhinum majus* (Harborne, J. B. Phytochemistry, 2, 327-334. 1963). Since the functionally unknown *Antirrhinum majus* glucosyltransferase AmUGTcg10 represented by SEQ ID NOs: 12 and 13, which were previously isolated, shows a high homology to PfUGT50 and S1UGT isolated in this EXAMPLE, AmUGTcg10 was also a candidate gene for enzyme analysis (Ono, E. et al., Proc. Natl. Acad. Sci. USA 103, 11075-11080. 2006).

The alignments of AmUGTcg10 from *Antirrhinum majus*, S1UGT from *Scutellaria laeteviolacea* v. *yakusimensis* and PfUGT50 from *Perilla frutescens* obtained above are shown in FIG. 1. In FIG. 1, Sb7GAT from *Scutellaria baicalensis* is also included.

3. Extraction and Purification of Flavonoids from the Leaves of *Perilla Frutescens*

(1) Purification of Scutellarein 7-Glucuronide

After 144.4 g of green-leaved perilla (Toyohashi Greenhouse Association in Aichi) corresponding to 200 leaves were ground into powders in liquid nitrogen, the powders were immersed in 1.5 L of 50% $CH_3CN$ and 0.1% HCOOH overnight and then filtered through a celite pad. The filtrate was concentrated under reduced pressure. The concentrate was loaded on 600 ml of CHP-20P and stepwise eluted twice with 300 ml each of water, 10, 20, 30, 40 and 50% $CH_3CN/H_2O$. Each fraction from 10%-2 to 50%-1 in which elution of polyphenols was observed was concentrated, frozen and dried, which was subjected to HPLC analysis. The yield was 10%-2 (12.1 mg), 20%-1 (52.5 mg), 20%-2 (122.4 mg), 30%-1 (227.5 mg), 30%-2 (262.8 mg), 40%-1 (632.4 mg), 40%-2 (192.0 mg) and 50%-1 (113.2 mg). In the 40%-1 fraction, rosmarinic acid was contained in a high purity and the other fractions all contained flavones. The 30%-2 fraction was purified by preparatory HPLC below to give 16 mg of scutellarein 7-glucuronide.

Conditions for Preparatory HPLC

Column: Develosil C-30-UG5, 20 mm×250 mm

Moving phase: A-0.1% TFA, B-0.05% TFA/90% $CH_3CN$

Flow rate: 6 ml/min.

Gradient: B20→B60% (100 min), B60% iso (20 min)

Detected: A280 nm (2) Hydrolysis of Scutellarein 7-Glucuronide and Purification of Aglycone From scutellarein 7-glucuronide obtained in (1) above, 3 mg was dissolved in 100 µL of DMSO and the solution was divided into 15 ml falcon tubes in half. To each tube 10 mL of $H_2O$, 2.5 mL of 0.2M Na acetate buffer (pH5.0) and 0.8 ml of β-glucronidase/arylsulfatase (EC3.2.1.31/EC3.1.6.1, Roche Diagnostics GmbH) solution were added, followed by incubation at 37° C. for 2 hours. After completion of the reaction, the solution mixture was loaded onto Sep-Pak-C 18 (20 cc). After washing with 20 ml of water and then with 20 ml of 10% EtOH to remove salts and proteins, the aglycone formed was eluted with 40 ml of 80% $CH_3CN$+0.05% TFA. The eluate was concentrated and freeze dried. This fraction was purified by preparatory HPLC below to give 0.4 mg of scutellarein (aglycone).

Conditions for Preparatory HPLC
    Column: Develosil C-30-UG5, 20 mm×250 mm
    Moving phase: A-0.1% TFA, B-0.05% TFA/90% $CH_3CN$
    Flow rate: 6 ml/min.
    Gradient: B15→B70% (60 min), B70% iso (10 min)
    Detected: A330 nm

4. Expression of Recombinant *Perilla Frutescens* Glucosyltransferase and Its Activity Assay (1) Construction of Expression Vector cDNAs bearing the full-length ORF of 3 glucosyltransferases of PfUGT50 from *Perilla frutescens*, S1UGT from *Scutellaria laetevioiacea* v. *yakusimensis* and AmUGTcg10 from *Antirrhinum majus*, having a high homology to each other, were amplified using the primer sets specific to the respective genes (PfUGT50, SEQ ID NOs: 14-15; S1UGT, SEQ ID NOs: 16-17; AmUGTcg10, SEQ ID NOs: 18-19). cDNAs synthesized using total RNAs extracted from the leaves of *Perilla frutescens*, the radix of *Scutellaria laetevioiacea* v. *yakusimensis* and the petals of *Antirrhinum majus* were used as templates, respectively.

```
SEQ ID NO: 14: PfUGT50-fw:
5'-AAACATATGGAAGGCGTCATACTTC-3'

(the underlined is the NdeI site)

SEQ ID NO: 15: PfUGT50-rv:
5'-TTTTGATCATTAATCACGAGTTACGGAATC-3'

(the underlined is the BclI site)

SEQ ID NO: 16: S1UGT-fw:
5'-AAACATATGGAGGACACGATTGTTATC-3'

(the underlined is the NdeI site)

SEQ ID NO: 17: S1UGT-rv:
5'-TTCATATGTCAATCCCTCGTGGCCAGAAG-3'

(the underlined is the NdeI site)

SEQ ID NO: 18: AmUGTcg10-fw:
5'-AAACATATGGAGGACACTATCGTTCTC-3'

(the underlined is the NdeI site)

SEQ ID NO: 19: AmUGTcg10-rv:
5'-TTGGATCCTTAAGAAACCACCATATCAAC-3'

(the underlined is the BamHI site)
```

PCR (KOD-Plus-, TOYOBO) was carried out, after reacting at 94° C. for 2 minutes, by repeating 35 cycles with each cycle consisting of reacting at 94° C. for 15 seconds, 50° C. for 30 seconds and 68° C. for 1.5 minutes. The amplified DNA fragments were subcloned into pCR-Blunt II-TOPO vector (Zero Blunt TOPO PCR Cloning Kit, Invitrogen) and the nucleotide sequence was confirmed by an ABI 3100 Avant (Applied Biosystems). With respect to PfUGT50, unmethylated plasmid was obtained by transformation of the positive strains obtained. The plasmids obtained were digested with NdeI and BclI in the case of PfUGT50, with NdeI in S1UGT and with NdeI and BamHI in AmUGTcg10, respectively. The resulting DNA fragments of about 1.5 kb were ligated into pET-15 digested with NdeI and BamHI in the case of PfUGT50 and AmUGTcg10 and with NdeI in the case of S1UGT.

(2) Culture of Recombinant *Escherichia Coli* and Purification of Protein

*Escherichia coli* BL21 (DE3) was transformed with each plasmid obtained in 4-(1) above. The transformant obtained was shake cultured overnight at 37° C. in 4 ml of LB medium (10 g/l tryptone, 5 g/l yeast extract, 1 g/l NaCl) supplemented with 50 µg/ml of ampicillin. The culture broth, 4 ml, which reached the stationary phase, was inoculated into 80 ml of the medium with the same composition, followed by shake culture at 37° C. When the cell turbidity ($OD_{600}$) reached approximately 0.5, 0.4 mM IPTG (isopropyl-β-thiogalactopyranoside) in a final concentration was added to the medium, followed by shake culture at 22° C. for 20 hours. All of the subsequent procedures were performed at 4° C. The transformants cultured were centrifuged (7,000×g, 15 mins.) to collect the cells, and 2 ml/g cell of Buffer S (20 mM sodium phosphate buffer (pH 7.4), 20 mM imidazole, 0.5 M NaCl, 14 mM β-mercaptoethanol) was added to the cells for suspension. Subsequently, ultrasonication was performed (15 secs.× 8) followed by centrifugation (15,000×g, 10 mins.). To the supernatant obtained, 0.12% (w/v) polyethyleneimine in a final concentration was added to suspend the cells, which was then allowed to stand for 30 minutes. The mixture was centrifuged (15,000×g, 10 mins.) and the supernatant was recovered as a crude enzyme solution. The crude enzyme solution was applied to His SpinTrap (GE Healthcare), which had been equilibrated with Buffer S, and centrifuged (70×g, 30 secs.). After washing with 600 µl of Buffer S, the protein bound to the column was stepwise eluted with 600 µl each of Buffer S containing 100, 200 and 500 mM imidazole. The buffer in each fraction eluted was replaced by 20 mM potassium phosphate buffer (pH 7.5) containing 14 mM β-mercaptoethanol, using Microcon YM-30 (Amicon). As a result of SDS-PAGE analysis, the protein of expected size was confirmed in the fractions eluted with 100 mM and 200 mM imidazole. These fractions were mixed and used for analysis. The objective proteins were not single in these fractions.

(3) Enzyme Reaction and Conditions for HPLC Analysis

Standard reaction conditions are as follows. A reaction solution (2 mM UDP-glucuronic acid, 100 µM glycosyl acceptor substrate, 50 mM potassium phosphate buffer (pH 7.5), enzyme solution), 50 µl, was prepared and the enzyme solution was added to initiate the reaction at 30° C. for 30 minutes. The reaction was stopped by adding 50 µl of 0.5% TFA in $CH_3CN$ and provided for HPLC analysis. The conditions for HPLC are as follows: column, Develosil C30-UG-5 (4.6×150 mm); eluant A, 0.1% TFA/$H_2O$; eluant B, 0.08% TFA/90% $CH_3CN$; conditions A for elution (except for aurone, catechin, coumarine and phenylpropanoid), 0 min/ 5% B→18 min/100% eluant B'18.1 min/5% B→25 min/5% B; conditions B for elution (aurone, catechin, coumarine and phenylpropanoid), 0 min/5% B→20 min/50% eluant B→20.5 min/5% B→25 min/5% B; flow rate, 1 ml/min;

detection wavelength: 280 and 350 nm. Respective characterizations and results are shown below.

Analysis of Glycosyl Acceptor Substrate Specificity

Figure 3:
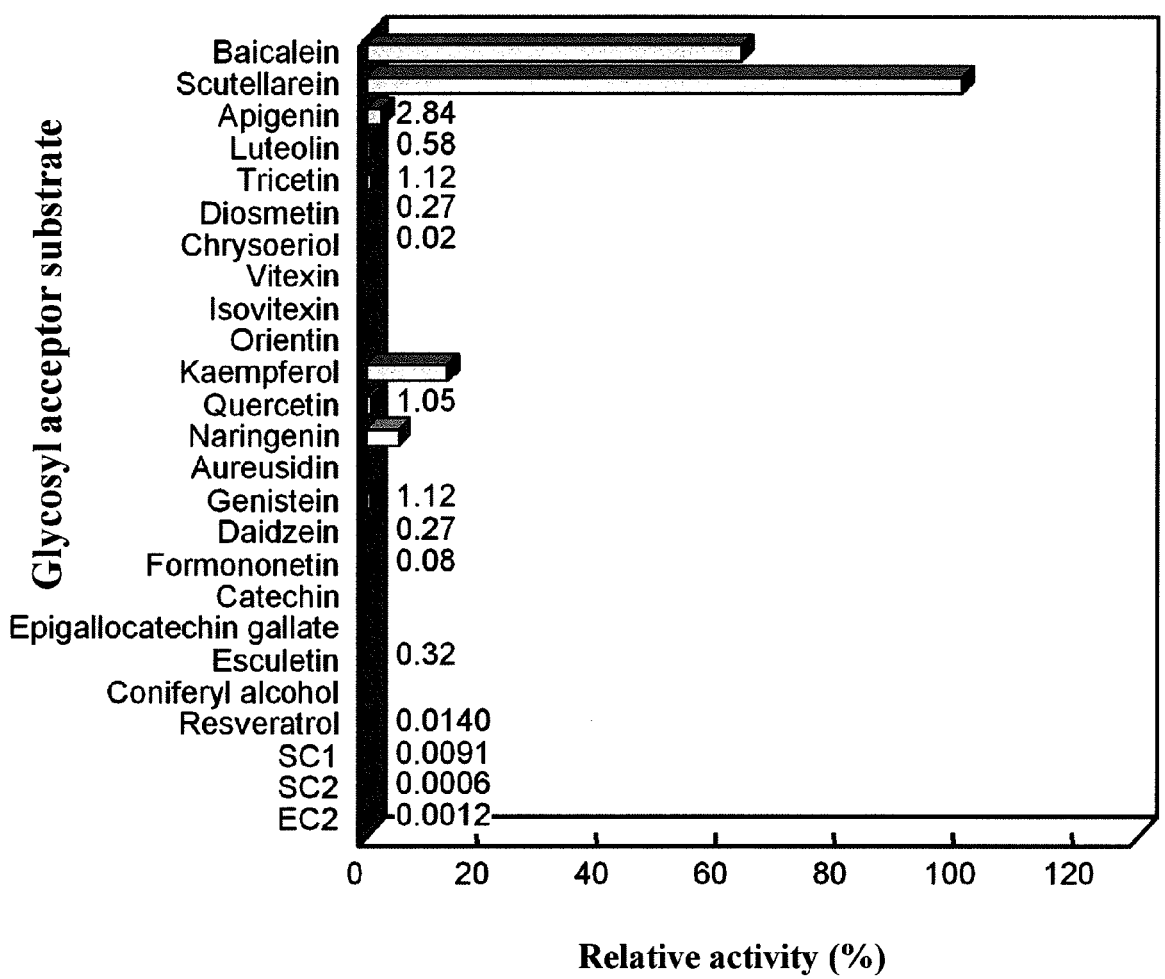
FIG. 3 shows the results of analysis on the specificity of glycosyl acceptor substrates for S1UGT.
Figure 4:
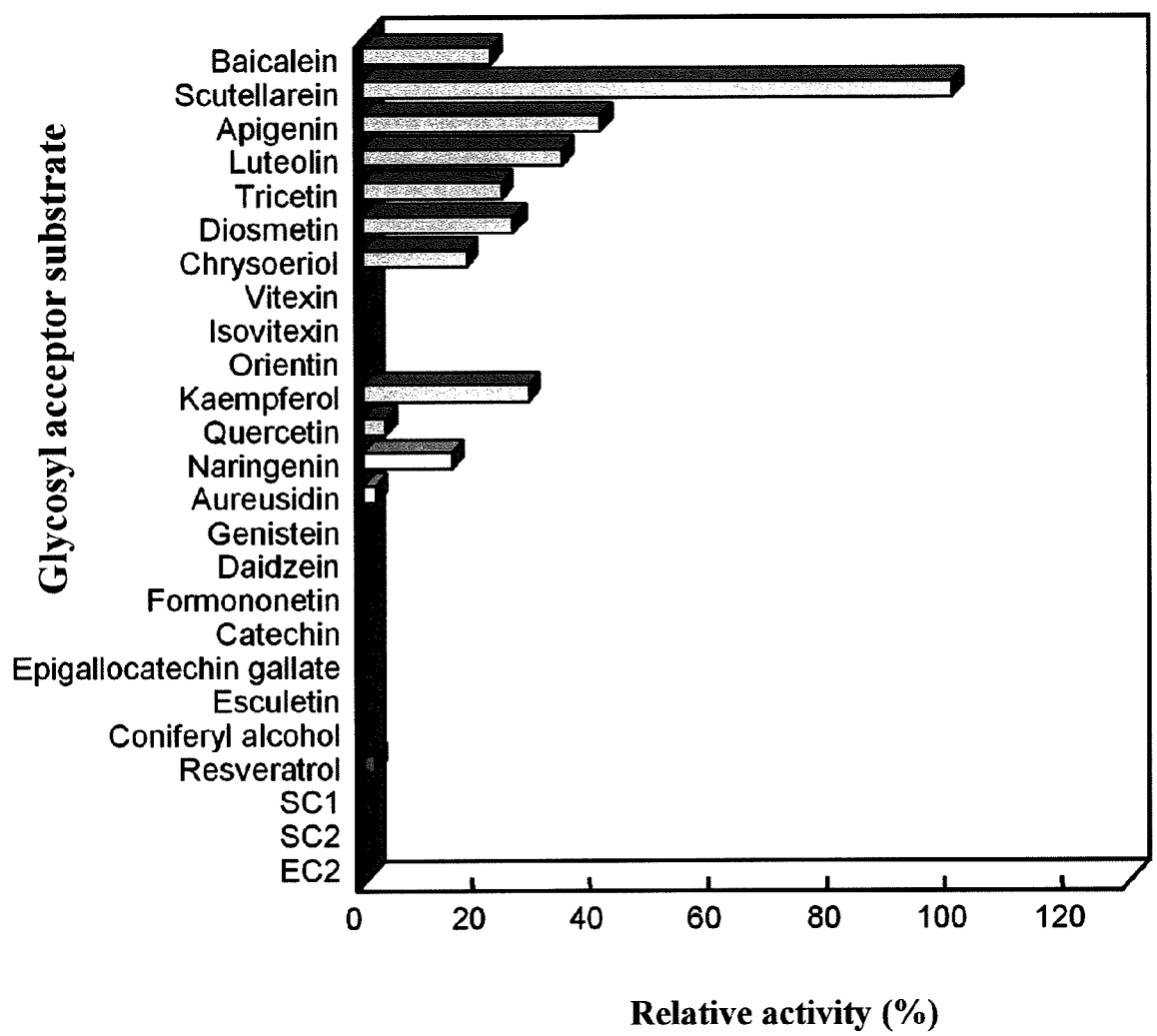
FIG. 4 shows the results of analysis on the specificity of glycosyl acceptor substrates for AmUGTcg10.

In accordance with the method described above, the specificity of various glycosyl acceptor substrates was analyzed (FIGS. 2 to 4).

FIG. 2 shows the results of analysis on the specificity of glycosyl acceptor substrates for PfUGT50. In FIG. 2, the relative activity to each substrate is shown, taking the activity to scutellarein as 100%. As a result of the analysis, PfUGT50 showed the highest activity to scutellarein and reacted well with flavones other than glycosides (baicalein (relative activity to scutellarein, 73%), apigenin (44%), luteolin (41%), tricetin (87.9%), diosmetin (62%) and chrysoeriol (18%)). Furthermore, PfUGT50 showed the activity also to flavonols (quercetin (26%), myricetin (9%) and kaempferol (3%)) and flavanones (naringenin (3%)) and (aureusidin (40%)). However, PfUGT50 showed no activity to flavone C-glycosides (vitexin, isovitexin and orientin), isoflavones (genistein, daidzein and formononetin), catechins (catechin and epigallocatechin gallate), coumarines (esculetin) and phenylpropanoids (coniferyl alcohol). In HPLC, the reaction products of scutellarein, baicalein, apigenin and quercetin coincided in terms of retention time with the respective 7-glucuronosylated products.

FIG. 3 shows the results of analysis on the specificity of glycosyl acceptor substrates for S1UGT. In FIG. 3, the relative activity to each substrate is shown, taking the activity to scutellarein as 100%. As a result of the analysis, S1UGT showed the highest activity to scutellarein but lower activities to flavones (apigenin (3%), luteolin (0.6%), tricetin (1.1%), diosmetin (0.3%), chrysoeriol (0.02%)) other than baicalein (relative activity to scutellarein, 63%). The activities to flavonols (quercetin (1%), kaempferol (14%)), flavanones (naringenin (6%)), isoflavones (genistein (1%), daidzein (0.3%) and formononetin (0.08%)) and coumarines (esculetin (0.3%)) were low. S1UGT showed no activity on flavone C-glycosides (vitexin, isovitexin and orientin), aurones (aureusidin), catechins (catechin and epigallocatechin gallate) or phenylpropanoids (coniferyl alcohol). In other words, it was suggested that modification at the ortho-position of the 7 position of flavonoids would be important for the activity of S1UGT. In HPLC, the reaction products of scutellarein, baicalein and apigenin coincided in terms of retention time with the respective 7-glucuronosylated products. On the other hand, pluralities of the products were detected with quercetin and one of them coincided in terms of retention time with the 7-glucuronosylated product.

FIG. 4 shows the results of analysis on the specificity of glycosyl acceptor substrates for AmUGTcg10. In FIG. 4, the relative activity to each substrate is shown, taking the activity to scutellarein as 100%. As a result of the analysis, AmUGTcg10 showed the highest activity to scutellarein and reacted also with flavones other than glycosides (baicalein (relative activity to scutellarein, 22%), apigenin (40%), luteolin (34%), tricetin (23.8%), diosmetin (26%) and chrysoeriol (18%)). AmUGTcg10 also showed the activities to flavonols (quercetin (4%) and kaempferol (28%)), flavanones (naringenin (15%)) and aurones (aureusidin (2%)). However, AmUGTcg10 showed no activity to flavone C-glycosides (vitexin, isovitexin and orientin), isoflavones (genistein, daidzein and formononetin), catechins (catechin and epigallocatechin gallate), coumarines (esculetin) and phenylpropanoids (coniferyl alcohol). In HPLC, the reaction products of scutellarein, baicalein, apigenin and quercetin coincided in terms of retention time with the respective 7-glucuronosylated products.

The foregoing results reveal that PfUGT50 and AmUGTcg10 show a low specificity, whereas S1UGT showed a high specificity, to flavonoids such as flavones, etc. The results further reveal that PfUGT50 derived from $Perilla\ frutescens$ shows a particularly low specificity, i.e., is an enzyme with a broader range of substrate specificity.

Analysis of Glycosyl Donor Substrate Specificity

Using apigenin as a glycosyl acceptor substrate, specificity to various UDP-activated glycosyl donors was analyzed. As a result, PfUGT50, S1UGT and AmUGTcg10 showed the activity only to UDP-glucuronic acid but showed no activity on UDP-glucose and UDP-galactose.

The foregoing results reveal that these enzymes are 7-glucuronosyltransferase highly specific for flavones (flavone 7-glucuronosyltransferase).

Analysis of pH and Temperature Characteristics

Temperature stability was analyzed as follows. An enzyme solution was treated at 15 to 55° C. for an hour and then cooled to 4° C. Using the sample cooled, the residual activity was determined under standard reaction conditions. After 167 mM final concentration of a buffer solution (pH 4, 4.5, 5, Acetate-NaOH; pH 5.5, 6, 6.5, 7, 7.5, $NaH_2PO_4$-NaOH; pH 8, 8.5, 9, Tris-HCl) was added to the enzyme solution, the mixture was treated at 4° C. for an hour and then 500 mM final concentration of potassium phosphate buffer (pH 7.5) was added thereto. Using the sample treated, the residual activity was determined under standard reaction conditions. The reaction was performed under standard reaction conditions where the reaction temperature was set at 10 to 55° C. to analyze the reaction temperature dependency. Reaction pH dependency was analyzed under standard reaction conditions using a buffer solution (pH 4, 4.5, 5, Acetate-NaOH; pH 5.5, 6, 6.5, 7, 7.5, $NaH_2PO_4$—NaOH; pH 8, 8.5, 9, Tris-HCl) in place of potassium phosphate buffer (pH 7.5). As a result of the foregoing analyses, PfUGT50 was stable at pH ranging from 7 to 9 and showed the maximum catalytic activity at pH between 7 and 8 but showed little activity in an acidic region. PfUGT50 was stable at 30° C. or lower (an hour, pH 7.5) and the reaction optimum temperature was 30° C. in the activity assay for 30 minutes. S1UGT was stable at pH ranging from 4.5 to 8 and showed the maximum catalytic activity at pH between 7 and 8 but showed little activity in an acidic region. This enzyme was stable at 40° C. or lower (an hour, pH 7.5) and the reaction optimum temperature was 35° C. in the activity assay for 30 minutes. AmUGTcg10 was stable at pH ranging from 7.5 to 9.5 and showed the maximum catalytic activity at pH between 8.5 and 9.5 but showed little activity in an acidic region. This enzyme was stable at 30° C. or lower (an hour, pH 7.5) and the reaction optimum temperature was 45° C. in the activity assay for 30 minutes. These properties were similar to known GT involved in plant secondary metabolism.

5. Results

PfUGT50 derived from $Perilla\ frutescens$, S1UGT derived from $Scutellaria\ laeteviolacea$ v. $yakusimensis$ and AmUGTcg10 derived from Scrophulariaceae, $Antirrhinum\ majus$, which are structurally similar as described above, were identified. Glucosyltransferases from PfUGT50 and AmUGTcg10 had a broad glycosyl acceptor substrate specificity as compared to Sb7GAT from $Scutellaria\ baicalensis$ and had the 7-glucuronosyl transfer activity of various flavonoids such as flavones, flavonols, aurones, etc. On the other hand, S1UGT showed a substrate specificity similar to Sb7GAT. By using these glucosyltransferases, the 7-position of flavonoids can be glucuronidated at a low cost.

Therefore, glucuronides including quercetin 7-glucronide, which are present in vivo, can be mass-produced in vitro, which enables to assess their physiological activities.

EXAMPLE 2

1. Outline of Example 2

In this EXAMPLE, SiUGT23 highly homologous to S1UGT from *Scutellaria laeteviolacea* v. *yakusimensis* and AmUGTcg12 from *Antirrhinum majus* was identified from Lamiales Pedaliaceae *Sesamum indicum* and it was confirmed that its *Escherichia coli* expression protein had the glucuronosyl transfer activity to scutellarein and luteolin.

2. Identification of SiUGT23 Gene

Paying attention to the sequence conservation of 7-glucuronosyltransferase genes (UGT genes) of flavonoids from *Scutellaria laeteviolacea* v. *yakusimensis* and *Antirrhinum majus*, genes having a high homology to these genes were searched, and sesame UGT gene SiUGT23 showing a high homology to these UGT genes was found also in Lamiales Pedaliaceae *Sesamum indicum*. Since SiUGT23 isolated from the sesame cDNA library had no full-length sequence, the full-length sequence of SiUGT23 (SEQ ID NOs: 22 and 23) was determined by the RACE method described in EXAMPLE 1, 2 (3), using the primers of SEQ ID NOs: 20 and 21 described below.

```
SEQ ID NO: 20: GR-SiUGT23-Rv
5'-GGCCAAACGCGCCGGAGCTGATGTAGA-3'

SEQ ID NO: 21: SiUGT23-nest-Rv
5'-AGTGGGTATATTCAAGCCTGT-3'
```

3. Expression of SiUGT23 Derived from *Sesamum Indicum* and Its Activity Assay cDNA containing full-length ORF of SiUGT23 derived from *Sesamum indicum* was amplified by a gene-specific primer set (SEQ ID NOs: 24 and 25). cDNA synthesized using total RNA extracted from sesame seeds was used as a template. SiUGT23 was incorporated into *Escherichia coli* expression vector as in UGT of *Perilla frutescens, Scutellaria laeteviolacea* v. *yakusimensis* and *Antirrhinum majus* in EXAMPLE 1 and recombinant SiUGT23 protein was expressed in the same way to assay the enzyme activity.

```
SEQ ID NO: 24: SiUGT23-fw:
5'-CACCATATGGAAGACACCGTTGTCCTCTA-3'

(the underlined is the NdeI site)

SEQ ID NO: 25: SiUGT23-rv:
5'-GGATCCTAACATCACTCAAACCCGAGTCA-3'

(the underlined is the BamHI site)
```

Figure 5:
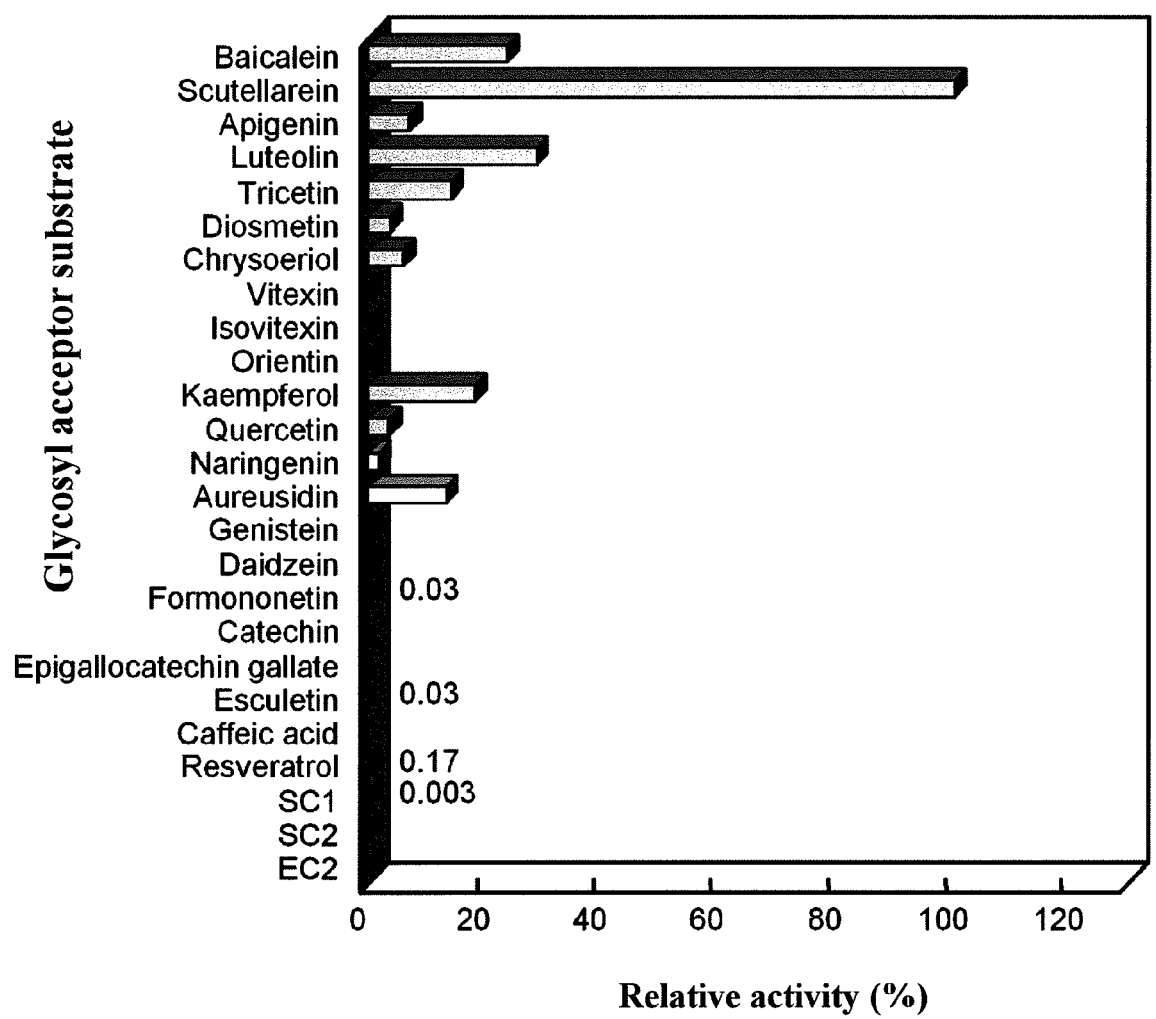
FIG. 5 shows the results of analysis on the specificity of glycosyl acceptor substrates for SiUGT23.

FIG. 5 shows the results of analysis on the specificity of glycosyl acceptor substrates for SiUGT23. In FIG. 5, the relative activity to each substrate is shown, taking the activity to scutellarein as 100%. As a result of the analysis, SiUGT23 showed the highest activity to scutellarein and reacted also with the following flavones (baicalein (relative activity to scutellarein (hereinafter the same), 24%), apigenin (7%), luteolin (29%), tricetin (14.0%), diosmetin (4%), chryseoriol (6%) and isovitexin (0.3%)). In addition, SiUGT23 showed the activities to flavonols (quercetin (4%) and kaempferol (18%)), flavanones (naringenin (2%)), aurones (aureusidin (13%)), coumarines (esculetin (0.03%)) and the following isoflavones (formononetin (0.03%)). However, SiUGT23 showed no activity to flavone C-glycosides (vitexin and orientin) other than isovitexin, isoflavones (genistein, Daidzein) other than formononetin, catechins (catechin and epigallocatechin gallate) and phenylpropanoids (caffeic acid). In HPLC, the reaction products of scutellarein, baicalein, apigenin and quercetin coincided in terms of retention time with the respective 7-glucuronosylated products.

The foregoing results revealed that SiUGT23 from *Sesamum indicum* was found to be a 7-glucuronosyltransferase of flavonoids showing a low specificity for flavonoids such as flavones, etc., as in PfGT50 from *Perilla frutescens* and AmUGTcg10 from *Antirrhinum majus*.

EXAMPLE 3

Using recombinant proteins of PfUGT50 derived from *Perilla frutescens*, S1UGT derived from *Scutellaria laeteviolacea* v. *yakusimensis* and AmUGTcg10 derived from *Antirrhinum majus* as well as recombinant protein of SiUGT23 derived from *Sesamum indicum*, the glucuronosyl transfer activities to stilbenes and lignans, which are plant polyphenols, were examined. The enzyme reaction was performed under the same conditions as described above, using resveratrol as a substrate for stilbenes and as substrates for lignans, (+)-pinoresinol, (+)-piperitol, (+)-sesaminol, (+)-secoisolariciresinol, (+)-sesamin catechol 1 (SC1), (+)-sesamin catechol 2 (SC2) and (+)-episesamin catechol 2 (EC2) (Nakai M, et al. (2003) J. Agric Food Chem. 51, 1666-1670).

Figure 6:
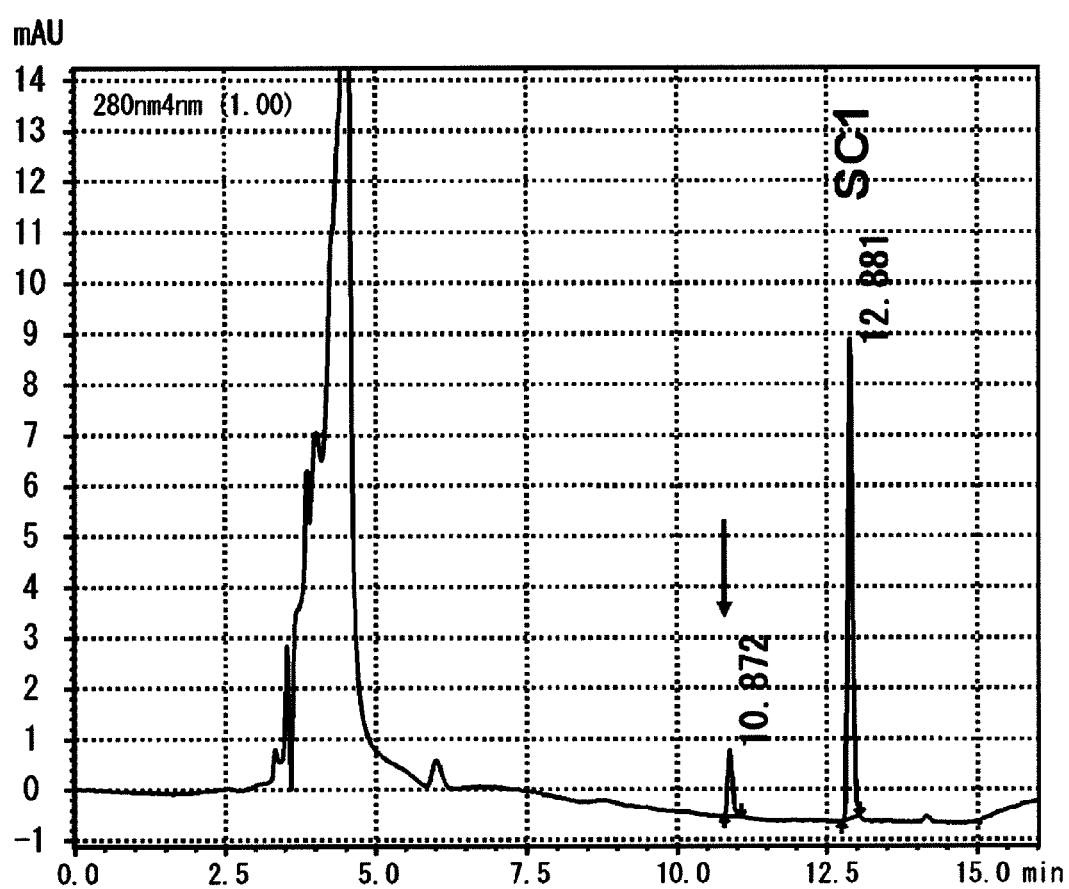
FIG. 6 shows the results of LC-MS analysis on the products in the reaction solution of S1UGT and SC1, wherein the arrows denote the products.
Figure 7:
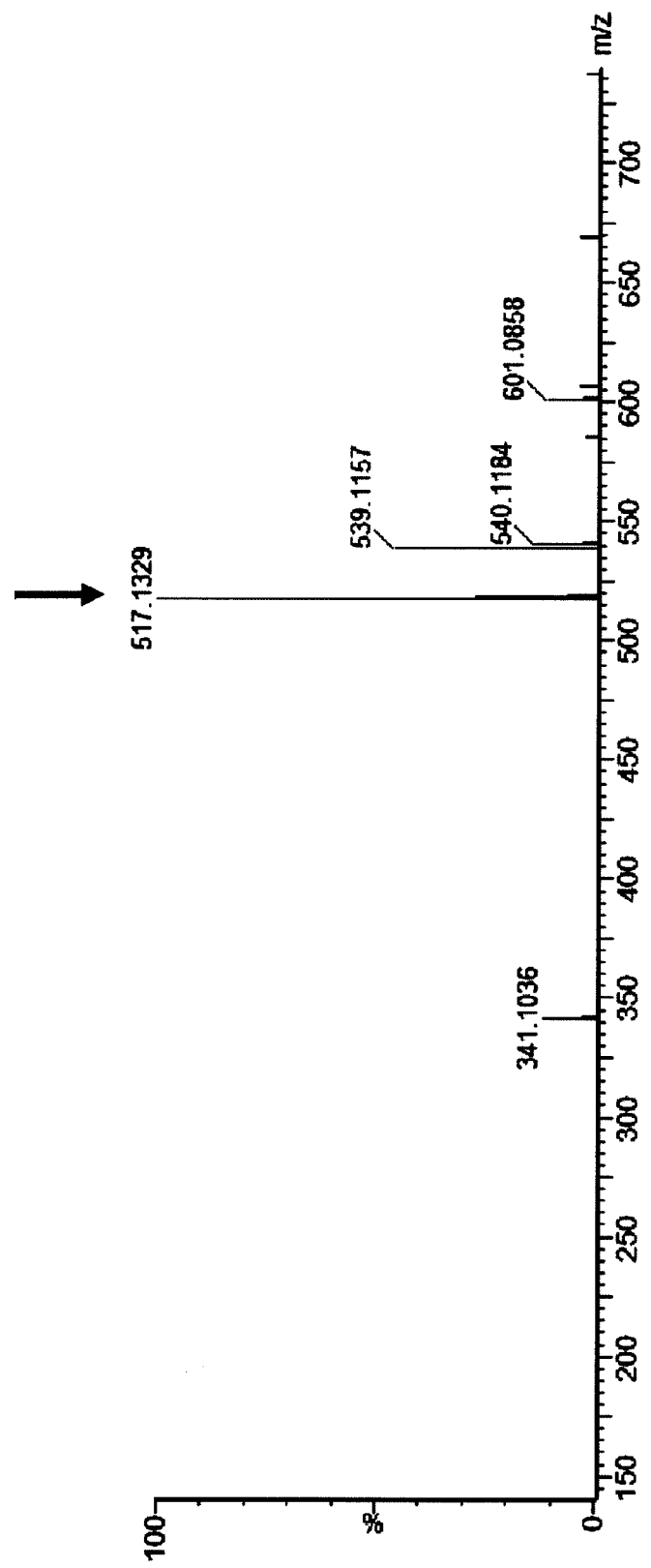
FIG. 7 shows the results of MS analysis on the products in the reaction of SC1 and S1UGT1.

As a result of the HPLC analysis, the products were obtained in all of the reaction solutions of PfUGT50 from *Perilla frutescens* a red-leaf variety, S1UGT from *Scutellaria laeteviolacea* v. *yakusimensis*, AmUGTcg10 from *Antirrhinum majus* and SiUGT23 from *Sesamum indicum* (cf., FIGS. 2 to 5). As for lignans, new products were obtained when SC1 and SC2 were used as substrates. As a result of the LC-MS analysis on the reaction of S1UGT with SC1 in which the largest numbers of the products were obtained, SC1 was eluted at R.T.=12.8 minutes and the reaction product was confirmed to be the SC1 monoglucuronide showing R.T.=10.8 minutes (FIG. 6) and m/z=517.1328 [M–H]⁻ ($C_{25}H_{25}O_{12}$, calcd. 517.1346, err. –2.5 ppm) (FIG. 7). LC-MS was performed under the following conditions.

Column: Develosil C30-UG3, 3 mm×150 mm

Moving phase: A; $H_2O$, B; $CH_3CN$, C; 2.5% HCOOH, 0.2 ml/min.

Gradient: B20%→B70% (10 mins.), B70% (5 mins.), C4%

Detected: A280 nm

MS conditions: Q-TOF-Premier (Micromass, Manchester, UK)

V mode, negative, capillary voltage: 2.3 KV, cone voltage: 45V

Based on the results above, it was confirmed that the glucuronides of stilbenes and lignans could be produced by using PfUGT50 from *Perilla frutescens* a red-leaf variety, S1UGT from *Scutellaria laeteviolacea* v. *yakusimensis*, AmUGTcg10 from *Antirrhinum majus* and SiUGT23 from *Sesamum indicum*, in addition to diverse flavonoids.

EXAMPLE 4

Figure 8:
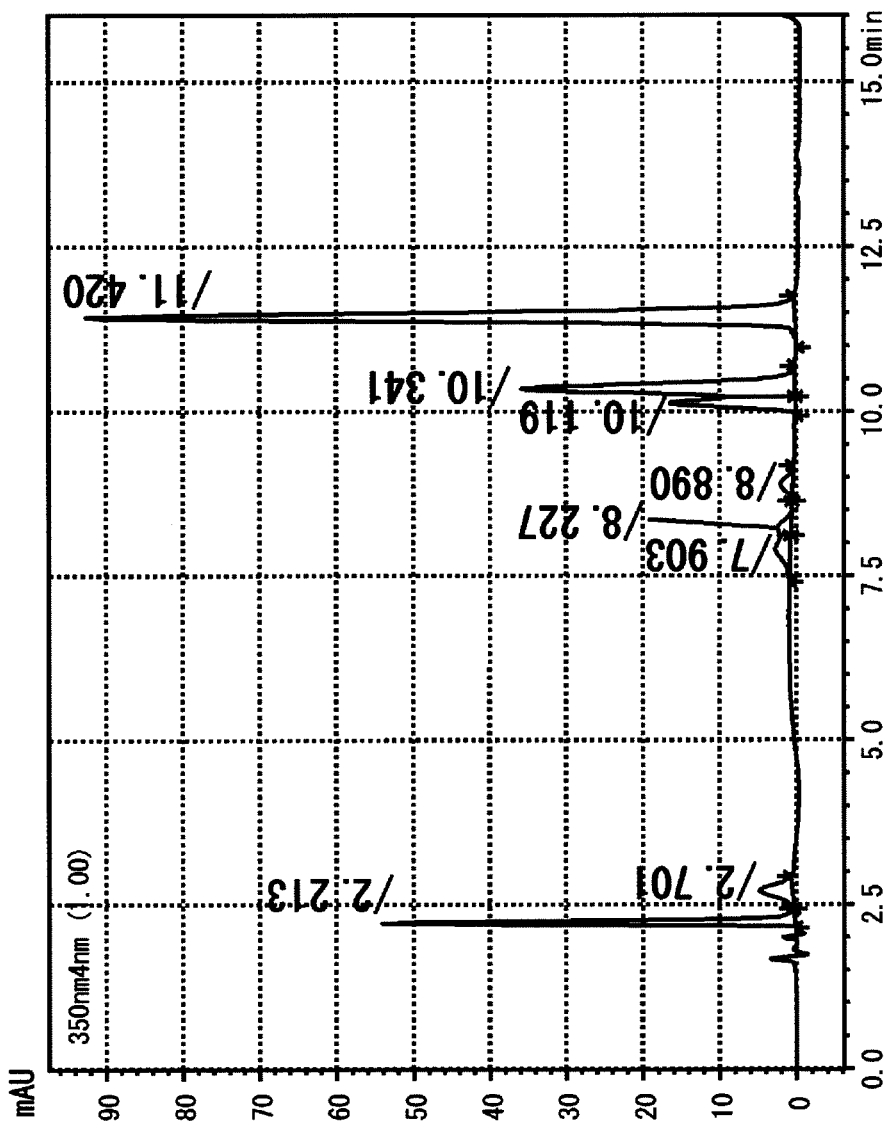
FIG. 8 shows the results of LC analysis on the products in the reaction of quercetin and S1UGT 1.

S1UGT derived from *Scutellaria laeteviolacea* v. *yakusimensis*, when reacted with quercetin (QU), gave a plurality of products in addition to the 7-glucuronic acid (FIG. 8).

They are characteristic products that are not found with SiUGT23 derived from *Sesamum indicum*, AmUGTcg10 derived from *Antirrhinum majus* and PfUGT50 derived from *Perilla frutescens*. As a result of the LC-MS analysis, quercetin diglucuronide showing m/z=653.1009 [M–H]− ($C_{27}H_{25}O_{19}$, calcd. 653.0990, err. 2.9 ppm), in which two glucuronic acids would be transferred to quercetin during the retention time of 7 to 9 minutes, was detected. During the retention time of 9 to 11 minutes, 3 types of quercetin monoglucuronides showing m/z=477.06 [M–H]−, in which one glucuronic acid would be transferred to quercetin, were detected. The component showing R.T.=10.12 minutes coincided with the reaction product with GAT of *Perilla frutescens*, which was purified and structurally analyzed, and was found to be quercetin 7-O-glucuronide. Furthermore, the component showing R.T.=10.34 minutes coincided with the major flavonol from grape leaves, which was purified and structurally analyzed, and was found to be quercetin 3-O-glucronide (Hmamouch, M. et al. (1996) Am. J. Enol Vitic., 47, 186-192). The component showing R.T.=11.3 minutes, which is the main reaction product, was found to be quercetin 3'-O-glucronide, after purification on reversed phase HPLC and structural analysis by NMR. It was confirmed that the 3 major peaks represented 7-, 3- and 3'-monoglucronides of quercetin, respectively.

The conditions for LC-MS are as follows.

Column: YMC-pack polymer C18, 2 mm×150 mm, 6 μm

Moving phase: A; $H_2O$, B; $CH_3CN$, C; 2.5% HCOOH, 0.2 ml/min.

Gradient: B10% B50% (10 minutes), B50% (5 minutes), C4%

Detected: A350 nm

MS conditions: Q-TOF-Premier (Micromass, Manchester, UK)

V mode, negative, capillary voltage: 3.0 KV, cone voltage: 30V

The foregoing results reveal that a variety of quercetin glucuronides can be obtained from quercetin by using S1UGT from *Scutellaria laeteviolacea* v. *yakusimensis*.

INDUSTRIAL APPLICABILITY

The UDP-glucuronosyltransferase of the present invention has a broad substrate specificity and is useful for the production of various glucuronides. The glucuronides produced are useful as reagents for inspecting the in vivo functions, antioxidants, etc.

The invention claimed is:

1. An isolated polynucleotide comprising:
   (a) nucleotides 1 to 1359 of SEQ ID NO: 4, nucleotides 1 to 1365 of SEQ ID NO: 10, or nucleotides 1 to 1371 of SEQ ID NO: 22, each of which encodes a protein having UDP-glucuronosyltransferase activity;
   (b) a polynucleotide that encodes a protein having UDP-glucuronosyltransferase activity and comprising SEQ ID NO: 5, 11, or 23;
   (c) a polynucleotide that encodes a protein having UDP-glucuronosyltransferase activity and having at least 95% sequence identity to SEQ ID NO: 5, 11, or 23;
   (d) a polynucleotide that encodes a protein having UDP-glucuronosyltransferase activity and that hybridizes under hybridization conditions comprising 5×SSC, 5×Denhardt's solution, 0.5% SDS, 50% formamide and 50° C. with a polynucleotide comprising a nucleotide sequence that is the full complement of nucleotides 1 to 1359 of SEQ ID NO: 4, nucleotides 1 to 1365 of SEQ ID NO: 10, or nucleotides 1 to 1371 of SEQ ID NO: 22; or,
   (e) a polynucleotide that encodes a protein having UDP-glucuronosyltransferase activity and that hybridizes under hybridization conditions comprising 5×SSC, 5×Denhardt's solution, 0.5% SDS, 50% formamide and 50° C. with a polynucleotide comprising a nucleotide sequence that is the full complement of a polynucleotide encoding a protein selected from the group consisting of SEQ ID NOs: 5, 11, and 23.

2. The isolated polynucleotide of claim 1, which comprises:
   a polynucleotide that encodes a protein having at least 98% sequence identity to SEQ ID NO: 5, 11, or 23, and having UDP-glucuronosyltransferase activity.

3. The isolated polynucleotide of claim 1, which comprises nucleotides 1 to 1359 of SEQ ID NO: 4.

4. The isolated polynucleotide of claim 1, which comprises nucleotides 1 to 1365 of SEQ ID NO: 10.

5. The isolated polynucleotide of claim 1, which comprises nucleotides 1 to 1371 of SEQ ID NO: 22.

6. The isolated polynucleotide of claim 1, which encodes a protein consisting of the amino acid sequence of SEQ ID NO: 5.

7. The isolated polynucleotide of claim 1, which encodes a protein consisting of the amino acid sequence of SEQ ID NO: 11.

8. The isolated polynucleotide of claim 1, which encodes a protein consisting of the amino acid sequence of SEQ ID NO: 23.

9. The isolated polynucleotide of claim 1, which is a DNA.

10. A vector comprising the polynucleotide of claim 1.

11. A transformant, wherein the polynucleotide of claim 1 is introduced.

12. A transformant, wherein the vector of claim 10 is introduced.

13. A method for producing a UDP-glucuronosyltransferase protein, comprising:
    culturing the transformant of claim 11; and
    separating the UDP-glucuronosyltransferase protein once accumulated in a culture.

* * * * *

UNITED STATES PATENT AND TRADEMARK OFFICE
CERTIFICATE OF CORRECTION

PATENT NO.       : 8,628,938 B2                                              Page 1 of 1
APPLICATION NO. : 12/678161
DATED            : January 14, 2014
INVENTOR(S)      : Ono et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Twenty-second Day of September, 2015

Michelle K. Lee
*Director of the United States Patent and Trademark Office*

SEQUENCE LISTING

```
<160> NUMBER OF SEQ ID NOS: 26

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaacatatgg cggtgctggc gaagttc                                            27

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttttgatcat taatcccgag tggcgtgaag                                         30

<210> SEQ ID NO 3
<211> LENGTH: 1326
<212> TYPE: DNA
<213> ORGANISM: Scutellaria sp.

<400> SEQUENCE: 3
atggcggtgc tggcgaagtt catcagcaag aaccacccct ccgtccccat catcattatc        60
agcaacgccc cggaatccgc cgccgcctcc gtggcggcca tcccttccat ctcctaccac       120
cgccttcccc tcccggagat ccctcccgac atgacaacag accgcgtgga gctcttcttc       180
gagctccctc gtctcagcaa ccctaaccct ctcactgctc tgcaacagat ctcccagaag       240
acaagaatca gagctgttat cctcgatttc ttctgcaacg cggcttttga ggttccgacc       300
agcctcaata tacccaccta ctactacttc agcgccggaa ctccaaccgc catcctcacc       360
```

```
ttgtacttcg aaaccatcga tgagaccatc cctgttgacc ttcaagacct caatgactat      420
gtcgacatcc ctggtttgcc gccgattcac tgcctcgata tccccgtggc tttgtcaccg      480
cgtaagagtc ttgtttacaa gagctccgtc gacatttcga agaacctgcg cagatcggca      540
ggcatcctcg ttaatggctt cgatgcactc gagtttagag ccataggaag ccatagtcaa      600
cggcctatgc atttcaaagg cccaactcct ccggtttact tcatcgggcc attggtcgga      660
gatgtcgaca ctaaggccgg cagcgaggag catgagtgtc tgagatggct tgatacacag      720
ccaagtaaga gtgtcgtctt cctttgtttt gggagaaggg gtgtcttctc tgctaagcag      780
ctgaaggaga cggcggcggc gttggagaac agtggccaca ggtttctctg gtcagtgaga      840
aacccaccgg agttgaagaa ggcgacgggg tccgatgagc cggacctgga tgagctgctg      900
cccgagggct tcctggagag aaccaaggat cggggtttcg tgataaagtc gtgggctcca      960
cagaaggagg tgctggctca cgactcggta ggtggattcg tgactcactg tgggcggagc     1020
tccgtgtctg aaggggtgtg gttcggagtg ccgatgatcg ggtggccggt ggacgcggag     1080
ctgaggttga atcgggcggt gatggtggat gatctgcagg tggcgctgcc gctggaggag     1140
gaggcgggtg ggttcgtgac ggcggctgag ttggagaaac gagttagaga gttgatggag     1200
acgaaggcgg ggaaggcggt gaggcaacga gtcaccgaac tgaaactctc cgccagggcg     1260
gcggtggcgg agaatggatc ctcgctaaat gatttgaaaa aatttcttca cgccactcgg     1320
gattaa                                                               1326

<210> SEQ ID NO 4
<211> LENGTH: 1490
<212> TYPE: DNA
<213> ORGANISM: Perilla frutescens
<220> FEATURE:
<221> NAME/KEY: CDS
<222> LOCATION: (1)..(1359)

<400> SEQUENCE: 4 atg gaa ggc gtc ata ctt ctt tac tca tcg gct gag cac ttg aac tcc        48
Met Glu Gly Val Ile Leu Leu Tyr Ser Ser Ala Glu His Leu Asn Ser
1               5                   10                  15 atg tta ttg ctc gcc acc ttc atc gcc aaa cac cat ccc tcc atc ccc        96
Met Leu Leu Leu Ala Thr Phe Ile Ala Lys His His Pro Ser Ile Pro
            20                  25                  30 atc aca atc ctt agc tcc gcc gac tac tca gcc gcc gcc tcc gtc tcc       144
Ile Thr Ile Leu Ser Ser Ala Asp Tyr Ser Ala Ala Ala Ser Val Ser
        35                  40                  45 acc ttg cct tcc att act tat cgc cgc ctc ccg ccc gtc gcg ata ccc       192
Thr Leu Pro Ser Ile Thr Tyr Arg Arg Leu Pro Pro Val Ala Ile Pro
    50                  55                  60 cct gac tca ata aag aac ccg gtc gaa gcc ttc ttc gaa atc cct cgt       240
Pro Asp Ser Ile Lys Asn Pro Val Glu Ala Phe Phe Glu Ile Pro Arg
65                  70                  75                  80 ctc caa aac cca aac ctt cgc gtc gcc ctc gaa gaa atc tcc cag aaa       288
Leu Gln Asn Pro Asn Leu Arg Val Ala Leu Glu Glu Ile Ser Gln Lys
                85                  90                  95 aca aga atc aga gca ttt gtg att gat ttc ttc tgc aat tcc gca ttt       336
Thr Arg Ile Arg Ala Phe Val Ile Asp Phe Phe Cys Asn Ser Ala Phe
            100                 105                 110 gaa gtc tcg acc agc ctc agc ata ccc act tac ttc tac gtc agc acc       384
Glu Val Ser Thr Ser Leu Ser Ile Pro Thr Tyr Phe Tyr Val Ser Thr
        115                 120                 125 ggt tcc gcc ggc gtc tgc atc ttc ctc tat ttc ccc acc acc gat gag       432
Gly Ser Ala Gly Val Cys Ile Phe Leu Tyr Phe Pro Thr Thr Asp Glu
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 130 |     |     |     | 135 |     |     |     | 140 |     |     |     |     |     |      |

```
acc gtt gct aca gac atc gga gac ttg cgt gat ttt ctt gaa ttc cct   480
Thr Val Ala Thr Asp Ile Gly Asp Leu Arg Asp Phe Leu Glu Phe Pro
145                 150                 155                 160 ggc tcc ccc att atc cac tca tcg gat ttg cca caa ctt aca ttt ttc   528
Gly Ser Pro Ile Ile His Ser Ser Asp Leu Pro Gln Leu Thr Phe Phe
                165                 170                 175 cgg cgg agt aat gtt ttc aag cac atg ttg gac act tcc aaa aac atg   576
Arg Arg Ser Asn Val Phe Lys His Met Leu Asp Thr Ser Lys Asn Met
            180                 185                 190 cag aaa tct tct ggg atc ctc aca aat gga ttc gac gct atg gag ttc   624
Gln Lys Ser Ser Gly Ile Leu Thr Asn Gly Phe Asp Ala Met Glu Phe
        195                 200                 205 aga gct aag gaa gct cta act aac ggc ctc tgc gtt ccc aac gga ccc   672
Arg Ala Lys Glu Ala Leu Thr Asn Gly Leu Cys Val Pro Asn Gly Pro
    210                 215                 220 act ccg ccg gtt tac tta gtt ggg cca cta gtt gcc gga agc aac gct   720
Thr Pro Pro Val Tyr Leu Val Gly Pro Leu Val Ala Gly Ser Asn Ala
225                 230                 235                 240 aaa aaa gac cac gag tgc ctg ctg tgg ctg gac aga cag cca agt aaa   768
Lys Lys Asp His Glu Cys Leu Leu Trp Leu Asp Arg Gln Pro Ser Lys
                245                 250                 255 agc gtg gtt ttc ctt tgt ttc ggc aga agg ggt ttg ttt tcc ggc aag   816
Ser Val Val Phe Leu Cys Phe Gly Arg Arg Gly Leu Phe Ser Gly Lys
            260                 265                 270 cag ttg aga gag atg gcg gtt gct cta gag aga agt ggc tac aga ttt   864
Gln Leu Arg Glu Met Ala Val Ala Leu Glu Arg Ser Gly Tyr Arg Phe
        275                 280                 285 ctg tgg tcg gtg cgg aat ccg ccg gaa aat cgt tcg ccg gcg gaa gac   912
Leu Trp Ser Val Arg Asn Pro Pro Glu Asn Arg Ser Pro Ala Glu Asp
    290                 295                 300 cct gat ttg gac gag ctt ttg cct gag ggt ttt ctg gag aga act aaa   960
Pro Asp Leu Asp Glu Leu Leu Pro Glu Gly Phe Leu Glu Arg Thr Lys
305                 310                 315                 320 gat ata ggg ttt gtg gtg aag tcg tgg gcg cct cag aag gag gtg ctg   1008
Asp Ile Gly Phe Val Val Lys Ser Trp Ala Pro Gln Lys Glu Val Leu
                325                 330                 335 agt cat gac gcg gtg gcc ggc ttc gtg act cac tgt ggg agg agc tcg   1056
Ser His Asp Ala Val Ala Gly Phe Val Thr His Cys Gly Arg Ser Ser
            340                 345                 350 att ctg gaa gcg ctg gtg aat ggg aaa ccg atg atc ggt tgg cca atg   1104
Ile Leu Glu Ala Leu Val Asn Gly Lys Pro Met Ile Gly Trp Pro Met
        355                 360                 365 tac gcg gag cag agg atg aac aag gta ttc atg gtg gac gaa atg aag   1152
Tyr Ala Glu Gln Arg Met Asn Lys Val Phe Met Val Asp Glu Met Lys
    370                 375                 380 gta gcg ctg ccc ttg gag gag gag gag gat ggg ttc gtg acg gcg gtc   1200
Val Ala Leu Pro Leu Glu Glu Glu Glu Asp Gly Phe Val Thr Ala Val
385                 390                 395                 400 gag ttg gag aag cgg ctg aga cag ttg atg gag tcc aag aca ggg aga   1248
Glu Leu Glu Lys Arg Leu Arg Gln Leu Met Glu Ser Lys Thr Gly Arg
                405                 410                 415 gat gtt cgc cac cgt gtt gcc gaa atg aaa gcc gct gcc acg gcg gcg   1296
Asp Val Arg His Arg Val Ala Glu Met Lys Ala Ala Ala Thr Ala Ala
            420                 425                 430 atg gga gag aat ggt tcg gcg gtg gtt gct ttg cgg aag ttc att gat   1344
Met Gly Glu Asn Gly Ser Ala Val Val Ala Leu Arg Lys Phe Ile Asp
        435                 440                 445 tcc gta act cgt gat taaaggattt tacatatgtc gcttattaat taatatagta   1399
Ser Val Thr Arg Asp
```

```
tgtaacttag ttgttatttc gggaaatcta cccaagtcat tgagttcaat aatcaaatct    1459
tcctatgggc tatgccaaat taaaaataaa a                                   1490
```

<210> SEQ ID NO 5
<211> LENGTH: 453
<212> TYPE: PRT
<213> ORGANISM: Perilla frutescens

<400> SEQUENCE: 5

```
Met Glu Gly Val Ile Leu Leu Tyr Ser Ser Ala Glu His Leu Asn Ser
1               5                   10                  15

Met Leu Leu Ala Thr Phe Ile Ala Lys His His Pro Ser Ile Pro
            20                  25                  30

Ile Thr Ile Leu Ser Ser Ala Asp Tyr Ser Ala Ala Ser Val Ser
        35                  40                  45

Thr Leu Pro Ser Ile Thr Tyr Arg Arg Leu Pro Val Ala Ile Pro
    50                  55                  60

Pro Asp Ser Ile Lys Asn Pro Val Glu Ala Phe Phe Glu Ile Pro Arg
65                  70                  75                  80

Leu Gln Asn Pro Asn Leu Arg Val Ala Leu Glu Ile Ser Gln Lys
                85                  90                  95

Thr Arg Ile Arg Ala Phe Val Ile Asp Phe Phe Cys Asn Ser Ala Phe
            100                 105                 110

Glu Val Ser Thr Ser Leu Ser Ile Pro Thr Tyr Phe Tyr Val Ser Thr
        115                 120                 125

Gly Ser Ala Gly Val Cys Ile Phe Leu Tyr Phe Pro Thr Thr Asp Glu
130                 135                 140

Thr Val Ala Thr Asp Ile Gly Asp Leu Arg Asp Phe Leu Glu Phe Pro
145                 150                 155                 160

Gly Ser Pro Ile Ile His Ser Ser Asp Leu Pro Gln Leu Thr Phe Phe
                165                 170                 175

Arg Arg Ser Asn Val Phe Lys His Met Leu Asp Thr Ser Lys Asn Met
            180                 185                 190

Gln Lys Ser Ser Gly Ile Leu Thr Asn Gly Phe Asp Ala Met Glu Phe
        195                 200                 205

Arg Ala Lys Glu Ala Leu Thr Asn Gly Leu Cys Val Pro Asn Gly Pro
    210                 215                 220

Thr Pro Pro Val Tyr Leu Val Gly Pro Leu Val Ala Gly Ser Asn Ala
225                 230                 235                 240

Lys Lys Asp His Glu Cys Leu Leu Trp Leu Asp Arg Gln Pro Ser Lys
                245                 250                 255

Ser Val Val Phe Leu Cys Phe Gly Arg Arg Gly Leu Phe Ser Gly Lys
            260                 265                 270

Gln Leu Arg Glu Met Ala Val Ala Leu Glu Arg Ser Gly Tyr Arg Phe
        275                 280                 285

Leu Trp Ser Val Arg Asn Pro Pro Glu Asn Arg Ser Pro Ala Glu Asp
    290                 295                 300

Pro Asp Leu Asp Glu Leu Leu Pro Glu Gly Phe Leu Glu Arg Thr Lys
305                 310                 315                 320

Asp Ile Gly Phe Val Val Lys Ser Trp Ala Pro Gln Lys Glu Val Leu
                325                 330                 335

Ser His Asp Ala Val Ala Gly Phe Val Thr His Cys Gly Arg Ser Ser
            340                 345                 350
```

```
Ile Leu Glu Ala Leu Val Asn Gly Lys Pro Met Ile Gly Trp Pro Met
        355                 360                 365

Tyr Ala Glu Gln Arg Met Asn Lys Val Phe Met Val Asp Glu Met Lys
    370                 375                 380

Val Ala Leu Pro Leu Glu Glu Glu Asp Gly Phe Val Thr Ala Val
385                 390                 395                 400

Glu Leu Glu Lys Arg Leu Arg Gln Leu Met Glu Ser Lys Thr Gly Arg
                405                 410                 415

Asp Val Arg His Arg Val Ala Glu Met Lys Ala Ala Thr Ala Ala
            420                 425                 430

Met Gly Glu Asn Gly Ser Ala Val Val Ala Leu Arg Lys Phe Ile Asp
        435                 440                 445

Ser Val Thr Arg Asp
    450

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgggaggcaa accagggatc tcgacaa                                          27

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatcatccaa atctttaagg t                                                21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agaaggggtg tgttctccgc tgagcaa                                          27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaacagcggt cacagatttc t                                                21

<210> SEQ ID NO 10
<211> LENGTH: 1446
<212> TYPE: DNA
<213> ORGANISM: Scutellaria sp.
<220> FEATURE:
<221> NAME/KEY: CDS
```

<222> LOCATION: (1)..(1365)

<400> SEQUENCE: 10

| | | | | | | | | | | | | | | | | |
|---|---|---|---|---|---|---|---|---|---|---|---|---|---|---|---|---|
| atg | gag | gac | acg | att | gtt | atc | tac | acc | acg | ccg | gag | cac | ctg | aac | acc | 48 |
| Met | Glu | Asp | Thr | Ile | Val | Ile | Tyr | Thr | Thr | Pro | Glu | His | Leu | Asn | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atg | gcg | gtg | ctc | gcc | aag | ttc | atc | agc | aaa | cac | cac | ccc | tcc | gtc | ccc | 96 |
| Met | Ala | Val | Leu | Ala | Lys | Phe | Ile | Ser | Lys | His | His | Pro | Ser | Val | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| atc | ata | ctc | atc | agc | acc | gcc | gcc | gaa | tca | gcc | gcc | gcc | tcc | atc | gcc | 144 |
| Ile | Ile | Leu | Ile | Ser | Thr | Ala | Ala | Glu | Ser | Ala | Ala | Ala | Ser | Ile | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | gtc | ccc | tcc | atc | acc | tac | cac | cgc | ctc | ccc | ctc | ccc | gag | atc | cct | 192 |
| Ala | Val | Pro | Ser | Ile | Thr | Tyr | His | Arg | Leu | Pro | Leu | Pro | Glu | Ile | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| ccc | agc | ctg | aca | aag | gac | cgc | gtg | gag | ctc | ttc | ttc | gag | ctc | cct | cgt | 240 |
| Pro | Ser | Leu | Thr | Lys | Asp | Arg | Val | Glu | Leu | Phe | Phe | Glu | Leu | Pro | Arg | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ctc | agc | aac | cct | aat | ctc | cgc | ctt | gcc | ctg | caa | gag | atc | tcc | cag | aaa | 288 |
| Leu | Ser | Asn | Pro | Asn | Leu | Arg | Leu | Ala | Leu | Gln | Glu | Ile | Ser | Gln | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | aga | atc | aga | gcc | ttc | gtc | atc | gac | ttc | ttc | tgc | aac | gca | gct | ttt | 336 |
| Ala | Arg | Ile | Arg | Ala | Phe | Val | Ile | Asp | Phe | Phe | Cys | Asn | Ala | Ala | Phe | |
| | | 100 | | | | | 105 | | | | | 110 | | | | |

| | | | | | | | | | | | | | | | | |
|---|---|---|---|---|---|---|---|---|---|---|---|---|---|---|---|---|
| gag | gtt | tct | acc | agc | ctc | agt | ata | ccc | act | ttc | tac | tac | ttc | agc | tct | 384 |
| Glu | Val | Ser | Thr | Ser | Leu | Ser | Ile | Pro | Thr | Phe | Tyr | Tyr | Phe | Ser | Ser | |
| | | | | 115 | | | | | 120 | | | | | 125 | | |

| | | | | | | | | | | | | | | | | |
|---|---|---|---|---|---|---|---|---|---|---|---|---|---|---|---|---|
| gga | tcg | ccc | aca | gcc | acc | ctc | gtt | ctg | cac | ttc | caa | acc | ctt | gat | gag | 432 |
| Gly | Ser | Pro | Thr | Ala | Thr | Leu | Val | Leu | His | Phe | Gln | Thr | Leu | Asp | Glu | |
| | | 130 | | | | | 135 | | | | | 140 | | | | |

| | | | | | | | | | | | | | | | | |
|---|---|---|---|---|---|---|---|---|---|---|---|---|---|---|---|---|
| acc | atc | cct | ggt | gac | ctt | aaa | gat | ttg | gat | gat | ttt | gtc | gag | atc | cct | 480 |
| Thr | Ile | Pro | Gly | Asp | Leu | Lys | Asp | Leu | Asp | Asp | Phe | Val | Glu | Ile | Pro | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ggt | ttg | cct | ccc | att | tac | tcc | ctg | gat | atc | cct | gtt | gct | ctg | ctt | acg | 528 |
| Gly | Leu | Pro | Pro | Ile | Tyr | Ser | Leu | Asp | Ile | Pro | Val | Ala | Leu | Leu | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| cgt | cag | agc | ctt | gtt | tac | cag | agc | tct | gtt | gac | atc | tcg | aaa | aac | ctg | 576 |
| Arg | Gln | Ser | Leu | Val | Tyr | Gln | Ser | Ser | Val | Asp | Ile | Ser | Lys | Asn | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| cgc | aaa | tca | gca | ggc | ttc | ctt | gtt | aat | ggc | ttc | gat | gcc | ctc | gag | ttc | 624 |
| Arg | Lys | Ser | Ala | Gly | Phe | Leu | Val | Asn | Gly | Phe | Asp | Ala | Leu | Glu | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| aga | gct | aag | gaa | gcc | ata | gtc | aac | ggc | ctc | tgc | gtt | ccc | aat | ggc | ccg | 672 |
| Arg | Ala | Lys | Glu | Ala | Ile | Val | Asn | Gly | Leu | Cys | Val | Pro | Asn | Gly | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| act | cct | ccg | gtt | tac | ttc | atc | ggc | cca | ctc | gtc | gga | gat | gtc | gat | gcc | 720 |
| Thr | Pro | Pro | Val | Tyr | Phe | Ile | Gly | Pro | Leu | Val | Gly | Asp | Val | Asp | Ala | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| aaa | gcc | ggc | ggc | gaa | gag | cat | gaa | tgt | ctc | aga | tgg | ctt | gat | aca | cag | 768 |
| Lys | Ala | Gly | Gly | Glu | Glu | His | Glu | Cys | Leu | Arg | Trp | Leu | Asp | Thr | Gln | |
| | | | | 245 | | | | | 250 | | | | | 255 | | |

| | | | | | | | | | | | | | | | | |
|---|---|---|---|---|---|---|---|---|---|---|---|---|---|---|---|---|
| cca | agt | aag | agt | gtg | atc | ttc | ctt | tgc | ttt | ggc | aga | agg | ggt | gtg | ttc | 816 |
| Pro | Ser | Lys | Ser | Val | Ile | Phe | Leu | Cys | Phe | Gly | Arg | Arg | Gly | Val | Phe | |
| | | 260 | | | | | 265 | | | | | 270 | | | | |

| | | | | | | | | | | | | | | | | |
|---|---|---|---|---|---|---|---|---|---|---|---|---|---|---|---|---|
| tcc | gct | gag | caa | ctg | aag | gag | acg | gcg | gtg | gcg | ttg | gag | aac | agc | ggt | 864 |
| Ser | Ala | Glu | Gln | Leu | Lys | Glu | Thr | Ala | Val | Ala | Leu | Glu | Asn | Ser | Gly | |
| | | | 275 | | | | | 280 | | | | | 285 | | | |

| | | | | | | | | | | | | | | | | |
|---|---|---|---|---|---|---|---|---|---|---|---|---|---|---|---|---|
| cac | aga | ttt | ctg | tgg | tcg | gtg | cga | aac | cca | ccg | gag | atc | atg | aag | aac | 912 |
| His | Arg | Phe | Leu | Trp | Ser | Val | Arg | Asn | Pro | Pro | Glu | Ile | Met | Lys | Asn | |
| | | 290 | | | | | 295 | | | | | 300 | | | | |

```
tcc gat gag ccg gac ctg gat gag ctg ctg ccc gag ggg ttt ctg gag      960
Ser Asp Glu Pro Asp Leu Asp Glu Leu Leu Pro Glu Gly Phe Leu Glu
305                 310                 315                 320 aga acc aag gat cgg ggt ttc gtg atc aag tcg tgg gct ccg cag aag     1008
Arg Thr Lys Asp Arg Gly Phe Val Ile Lys Ser Trp Ala Pro Gln Lys
                325                 330                 335 gag gtg ctg agt cac gac tcg gtg ggg ggg ttc gtc act cac tgt ggg     1056
Glu Val Leu Ser His Asp Ser Val Gly Gly Phe Val Thr His Cys Gly
            340                 345                 350 cgg agc tcc att tcg gaa ggg gtg tgg ttt ggg gtg ccg atg atc ggg     1104
Arg Ser Ser Ile Ser Glu Gly Val Trp Phe Gly Val Pro Met Ile Gly
        355                 360                 365 tgg ccg gtg gac gcg gag cag aag ttg aat cga aca gtg ttg gtg gag     1152
Trp Pro Val Asp Ala Glu Gln Lys Leu Asn Arg Thr Val Leu Val Glu
370                 375                 380 gaa atg cag gtg gcg ctg ccg atg gag gag gcg gag ggt ggg ttc gtg     1200
Glu Met Gln Val Ala Leu Pro Met Glu Glu Ala Glu Gly Gly Phe Val
385                 390                 395                 400 acg gcg gct gag ctg gag aaa cga gtt aga gag ttg atg gag tcg aag     1248
Thr Ala Ala Glu Leu Glu Lys Arg Val Arg Glu Leu Met Glu Ser Lys
                405                 410                 415 gtg ggg aag gcg gtg agg caa cga gtc ggt gaa ttg aaa tgc tcg gcc     1296
Val Gly Lys Ala Val Arg Gln Arg Val Gly Glu Leu Lys Cys Ser Ala
            420                 425                 430 agg gca gcg gtg acg ggg aat gga tcc tcg cta agt gat ttt aaa aag     1344
Arg Ala Ala Val Thr Gly Asn Gly Ser Ser Leu Ser Asp Phe Lys Lys
        435                 440                 445 ttt ctt ctg gcc acg agg gat tgatcatata ctctccatct ccgtcattga        1395
Phe Leu Leu Ala Thr Arg Asp
450                 455 attcataaaa gtattttta gacaagtttt tgtgagagaa taagttaatc a             1446

<210> SEQ ID NO 11
<211> LENGTH: 455
<212> TYPE: PRT
<213> ORGANISM: Scutellaria sp.

<400> SEQUENCE: 11

Met Glu Asp Thr Ile Val Ile Tyr Thr Thr Pro Glu His Leu Asn Thr
1               5                   10                  15

Met Ala Val Leu Ala Lys Phe Ile Ser Lys His His Pro Ser Val Pro
                20                  25                  30

Ile Ile Leu Ile Ser Thr Ala Ala Glu Ser Ala Ala Ala Ser Ile Ala
            35                  40                  45

Ala Val Pro Ser Ile Thr Tyr His Arg Leu Pro Leu Pro Glu Ile Pro
        50                  55                  60

Pro Ser Leu Thr Lys Asp Arg Val Glu Leu Phe Phe Glu Leu Pro Arg
65                  70                  75                  80

Leu Ser Asn Pro Asn Leu Arg Leu Ala Leu Gln Glu Ile Ser Gln Lys
                85                  90                  95

Ala Arg Ile Arg Ala Phe Val Ile Asp Phe Cys Asn Ala Ala Phe
                100                 105                 110

Glu Val Ser Thr Ser Leu Ser Ile Pro Thr Phe Tyr Tyr Phe Ser Ser
            115                 120                 125

Gly Ser Pro Thr Ala Thr Leu Val Leu His Phe Gln Thr Leu Asp Glu
        130                 135                 140

Thr Ile Pro Gly Asp Leu Lys Asp Leu Asp Asp Phe Val Glu Ile Pro
145                 150                 155                 160
```

```
Gly Leu Pro Pro Ile Tyr Ser Leu Asp Ile Pro Val Ala Leu Leu Thr
              165                 170                 175

Arg Gln Ser Leu Val Tyr Gln Ser Ser Val Asp Ile Ser Lys Asn Leu
        180                 185                 190

Arg Lys Ser Ala Gly Phe Leu Val Asn Gly Phe Asp Ala Leu Glu Phe
    195                 200                 205

Arg Ala Lys Glu Ala Ile Val Asn Gly Leu Cys Val Pro Asn Gly Pro
210                 215                 220

Thr Pro Pro Val Tyr Phe Ile Gly Pro Leu Val Gly Asp Val Asp Ala
225                 230                 235                 240

Lys Ala Gly Gly Glu Glu His Glu Cys Leu Arg Trp Leu Asp Thr Gln
                245                 250                 255

Pro Ser Lys Ser Val Ile Phe Leu Cys Phe Gly Arg Arg Gly Val Phe
            260                 265                 270

Ser Ala Glu Gln Leu Lys Glu Thr Ala Val Ala Leu Glu Asn Ser Gly
        275                 280                 285

His Arg Phe Leu Trp Ser Val Arg Asn Pro Pro Glu Ile Met Lys Asn
    290                 295                 300

Ser Asp Glu Pro Asp Leu Asp Glu Leu Leu Pro Glu Gly Phe Leu Glu
305                 310                 315                 320

Arg Thr Lys Asp Arg Gly Phe Val Ile Lys Ser Trp Ala Pro Gln Lys
                325                 330                 335

Glu Val Leu Ser His Asp Ser Val Gly Gly Phe Val Thr His Cys Gly
            340                 345                 350

Arg Ser Ser Ile Ser Glu Gly Val Trp Phe Gly Val Pro Met Ile Gly
        355                 360                 365

Trp Pro Val Asp Ala Glu Gln Lys Leu Asn Arg Thr Val Leu Val Glu
    370                 375                 380

Glu Met Gln Val Ala Leu Pro Met Glu Glu Ala Glu Gly Gly Phe Val
385                 390                 395                 400

Thr Ala Ala Glu Leu Glu Lys Arg Val Arg Glu Leu Met Glu Ser Lys
                405                 410                 415

Val Gly Lys Ala Val Arg Gln Arg Val Gly Glu Leu Lys Cys Ser Ala
            420                 425                 430

Arg Ala Ala Val Thr Gly Asn Gly Ser Ser Leu Ser Asp Phe Lys Lys
        435                 440                 445

Phe Leu Leu Ala Thr Arg Asp
    450                 455

<210> SEQ ID NO 12
<211> LENGTH: 1374
<212> TYPE: DNA
<213> ORGANISM: Antirrhinum majus
<220> FEATURE:
<221> NAME/KEY: CDS
<222> LOCATION: (1)..(1371)

<400> SEQUENCE: 12 atg gag gac act atc gtt ctc tac gct tca gca gag cac ctt aac tcc      48
Met Glu Asp Thr Ile Val Leu Tyr Ala Ser Ala Glu His Leu Asn Ser
1               5                   10                  15 atg cta cta ctc ggc aaa ctc atc aac aaa cac cac ccc aca atc tcc     96
Met Leu Leu Leu Gly Lys Leu Ile Asn Lys His His Pro Thr Ile Ser
            20                  25                  30 gtc gcc att atc agc acc gcc cca aac gcc gcc gct agt tcc gtc gcc    144
Val Ala Ile Ile Ser Thr Ala Pro Asn Ala Ala Ala Ser Ser Val Ala
        35                  40                  45
```

| | | |
|---|---|---|
| gac gtg gcg gcc ata tct tat cag caa ctc aaa ccg gcc act ctc cct<br>Asp Val Ala Ala Ile Ser Tyr Gln Gln Leu Lys Pro Ala Thr Leu Pro<br>50                   55                          60 | | 192 |
| tcg gat cta acc aaa aac cca atc gag ctc ttc ttc gaa atc cca cgt<br>Ser Asp Leu Thr Lys Asn Pro Ile Glu Leu Phe Phe Glu Ile Pro Arg<br>65                   70                    75                  80 | | 240 |
| cta cat aat cct aac ttg ctc gaa gcg ctg gaa gaa ctg tca cta aaa<br>Leu His Asn Pro Asn Leu Leu Glu Ala Leu Glu Glu Leu Ser Leu Lys<br>                   85                    90                  95 | | 288 |
| tca aaa gta agg gca ttt gtg ata gat ttc ttt tgc aat ccc gca ttt<br>Ser Lys Val Arg Ala Phe Val Ile Asp Phe Phe Cys Asn Pro Ala Phe<br>100                          105                    110 | | 336 |
| gag gtt tcg act agc ttg aac ata ccc act tac ttc tat gtc agc agc<br>Glu Val Ser Thr Ser Leu Asn Ile Pro Thr Tyr Phe Tyr Val Ser Ser<br>           115                    120                    125 | | 384 |
| ggc gcg ttt ggg cta tgc ggg ttc ttg cat ttt ccg aca atc gac gaa<br>Gly Ala Phe Gly Leu Cys Gly Phe Leu His Phe Pro Thr Ile Asp Glu<br>130                          135                    140 | | 432 |
| act gtc gaa aaa gac atc ggt gaa ctg aac gat atc ttg gag atc ccg<br>Thr Val Glu Lys Asp Ile Gly Glu Leu Asn Asp Ile Leu Glu Ile Pro<br>145                    150                    155                  160 | | 480 |
| ggt tgc ccc ccg gtt ttg tcc tcg gat ttt ccg aaa ggt atg ttc ttt<br>Gly Cys Pro Pro Val Leu Ser Ser Asp Phe Pro Lys Gly Met Phe Phe<br>                     165                    170                    175 | | 528 |
| cgc aag agt aac act tac aag cat ttt tta gac acg gcg aaa aac atg<br>Arg Lys Ser Asn Thr Tyr Lys His Phe Leu Asp Thr Ala Lys Asn Met<br>                   180                    185                  190 | | 576 |
| agg aga gcg aaa ggg atc gtg gtg aac gcc ttc gac gcg atg gag ttc<br>Arg Arg Ala Lys Gly Ile Val Val Asn Ala Phe Asp Ala Met Glu Phe<br>           195                    200                    205 | | 624 |
| cga gct aaa gaa gcc ctc gtc aac aat ctg tgc gta ccc aat tcg cca<br>Arg Ala Lys Glu Ala Leu Val Asn Asn Leu Cys Val Pro Asn Ser Pro<br>210                          215                    220 | | 672 |
| act ccc cca gtt ttc tta gtc ggc cca ttg gtc gga gca agc aca act<br>Thr Pro Pro Val Phe Leu Val Gly Pro Leu Val Gly Ala Ser Thr Thr<br>225                    230                    235                  240 | | 720 |
| acg aaa acc aca aac gaa cag cac gaa tgc ttg aaa tgg ctg gac gtg<br>Thr Lys Thr Thr Asn Glu Gln His Glu Cys Leu Lys Trp Leu Asp Val<br>                   245                    250                  255 | | 768 |
| cag cca gac aga agc gtg atc ttc tta tgt ttc ggt agg agg ggt ttg<br>Gln Pro Asp Arg Ser Val Ile Phe Leu Cys Phe Gly Arg Arg Gly Leu<br>                   260                    265                  270 | | 816 |
| ttc tcc gca gac caa ttg aag gaa atc gca att ggt ctg gag aac agc<br>Phe Ser Ala Asp Gln Leu Lys Glu Ile Ala Ile Gly Leu Glu Asn Ser<br>275                          280                    285 | | 864 |
| ggc cac agg ttc ctg tgg tcc gtg cgt tgc cca cca agt aag cct aac<br>Gly His Arg Phe Leu Trp Ser Val Arg Cys Pro Pro Ser Lys Pro Asn<br>           290                    295                    300 | | 912 |
| tct tat aac act gat ccg gac ctg gac gag ctc ctg ccc gag ggg ttt<br>Ser Tyr Asn Thr Asp Pro Asp Leu Asp Glu Leu Leu Pro Glu Gly Phe<br>305                    310                    315                  320 | | 960 |
| ttg tcc agg acc gag acc cgg ggt ttc gtg atc aag tcg tgg gcg cct<br>Leu Ser Arg Thr Glu Thr Arg Gly Phe Val Ile Lys Ser Trp Ala Pro<br>                   325                    330                  335 | | 1008 |
| cag aag gag gtg ctg agc cat ggc gcg gtt gga ggg ttc gtg acg cac<br>Gln Lys Glu Val Leu Ser His Gly Ala Val Gly Gly Phe Val Thr His<br>               340                    345                  350 | | 1056 |
| tgt ggg agg agt tcg ata ttg gaa gcg gtg tcg ttt ggg gtg ccg atg<br>Cys Gly Arg Ser Ser Ile Leu Glu Ala Val Ser Phe Gly Val Pro Met<br>355                          360                    365 | | 1104 |

-continued

| | | | | | | | | | | | | | | |
|---|---|---|---|---|---|---|---|---|---|---|---|---|---|---|
| atc | ggg | tgg | ccg | ata | tac | gcg | gag | cag | agg | atg | aat | agg | gtg | ttc | atg | 1152 |
| Ile | Gly | Trp | Pro | Ile | Tyr | Ala | Glu | Gln | Arg | Met | Asn | Arg | Val | Phe | Met |
| | 370 | | | | 375 | | | | | 380 | | | | | |

| gtg | gag | gag | atg | aag | gtg | gcg | ttg | cag | ttg | gat | gag | gtg | gag | gaa | ggg | 1200 |
| Val | Glu | Glu | Met | Lys | Val | Ala | Leu | Gln | Leu | Asp | Glu | Val | Glu | Glu | Gly |
| 385 | | | | | 390 | | | | | 395 | | | | | 400 |

| ttc | gtg | gcg | gcg | gtg | gaa | ttg | gag | aag | aga | gtg | aag | gag | ttg | atg | gat | 1248 |
| Phe | Val | Ala | Ala | Val | Glu | Leu | Glu | Lys | Arg | Val | Lys | Glu | Leu | Met | Asp |
| | | | | 405 | | | | | 410 | | | | | 415 | |

| tcg | aag | aat | ggg | aga | gcg | gtt | agg | cag | aga | gtg | aag | gag | atg | aaa | gtg | 1296 |
| Ser | Lys | Asn | Gly | Arg | Ala | Val | Arg | Gln | Arg | Val | Lys | Glu | Met | Lys | Val |
| | | | 420 | | | | | 425 | | | | | 430 | | |

| gcg | gct | gag | gtg | gcg | gtt | gaa | aag | ggt | ggt | tcg | tca | gtt | gtg | gcg | ttg | 1344 |
| Ala | Ala | Glu | Val | Ala | Val | Glu | Lys | Gly | Gly | Ser | Ser | Val | Val | Ala | Leu |
| | | 435 | | | | | 440 | | | | | 445 | | | |

| caa | cgc | ttt | gtt | gat | atg | gtg | gtt | tct | taa | | | | | | | 1374 |
| Gln | Arg | Phe | Val | Asp | Met | Val | Val | Ser | | | | | | | |
| 450 | | | | | 455 | | | | | | | | | | |

<210> SEQ ID NO 13
<211> LENGTH: 457
<212> TYPE: PRT
<213> ORGANISM: Antirrhinum majus

<400> SEQUENCE: 13

Met Glu Asp Thr Ile Val Leu Tyr Ala Ser Ala Glu His Leu Asn Ser
1               5                   10                  15

Met Leu Leu Leu Gly Lys Leu Ile Asn Lys His His Pro Thr Ile Ser
            20                  25                  30

Val Ala Ile Ile Ser Thr Ala Pro Asn Ala Ala Ser Ser Val Ala
        35                  40                  45

Asp Val Ala Ala Ile Ser Tyr Gln Gln Leu Lys Pro Ala Thr Leu Pro
    50                  55                  60

Ser Asp Leu Thr Lys Asn Pro Ile Glu Leu Phe Phe Glu Ile Pro Arg
65                  70                  75                  80

Leu His Asn Pro Asn Leu Leu Glu Ala Leu Glu Glu Leu Ser Leu Lys
                85                  90                  95

Ser Lys Val Arg Ala Phe Val Ile Asp Phe Phe Cys Asn Pro Ala Phe
            100                 105                 110

Glu Val Ser Thr Ser Leu Asn Ile Pro Thr Tyr Phe Tyr Val Ser Ser
        115                 120                 125

Gly Ala Phe Gly Leu Cys Gly Phe Leu His Phe Pro Thr Ile Asp Glu
    130                 135                 140

Thr Val Glu Lys Asp Ile Gly Glu Leu Asn Asp Ile Leu Glu Ile Pro
145                 150                 155                 160

Gly Cys Pro Pro Val Leu Ser Ser Asp Phe Pro Lys Gly Met Phe Phe
                165                 170                 175

Arg Lys Ser Asn Thr Tyr Lys His Phe Leu Asp Thr Ala Lys Asn Met
            180                 185                 190

Arg Arg Ala Lys Gly Ile Val Val Asn Ala Phe Asp Ala Met Glu Phe
        195                 200                 205

Arg Ala Lys Glu Ala Leu Val Asn Asn Leu Cys Val Pro Asn Ser Pro
    210                 215                 220

Thr Pro Pro Val Phe Leu Val Gly Pro Leu Val Gly Ala Ser Thr Thr
225                 230                 235                 240

Thr Lys Thr Thr Asn Glu Gln His Glu Cys Leu Lys Trp Leu Asp Val
                245                 250                 255

Gln Pro Asp Arg Ser Val Ile Phe Leu Cys Phe Gly Arg Arg Gly Leu
            260                 265                 270

Phe Ser Ala Asp Gln Leu Lys Glu Ile Ala Ile Gly Leu Glu Asn Ser
        275                 280                 285

Gly His Arg Phe Leu Trp Ser Val Arg Cys Pro Pro Ser Lys Pro Asn
    290                 295                 300

Ser Tyr Asn Thr Asp Pro Asp Leu Asp Glu Leu Leu Pro Glu Gly Phe
305                 310                 315                 320

Leu Ser Arg Thr Glu Thr Arg Gly Phe Val Ile Lys Ser Trp Ala Pro
                325                 330                 335

Gln Lys Glu Val Leu Ser His Gly Ala Val Gly Gly Phe Val Thr His
            340                 345                 350

Cys Gly Arg Ser Ser Ile Leu Glu Ala Val Ser Phe Gly Val Pro Met
        355                 360                 365

Ile Gly Trp Pro Ile Tyr Ala Glu Gln Arg Met Asn Arg Val Phe Met
    370                 375                 380

Val Glu Glu Met Lys Val Ala Leu Gln Leu Asp Glu Val Glu Glu Gly
385                 390                 395                 400

Phe Val Ala Ala Val Glu Leu Glu Lys Arg Val Lys Glu Leu Met Asp
                405                 410                 415

Ser Lys Asn Gly Arg Ala Val Arg Gln Arg Val Lys Glu Met Lys Val
            420                 425                 430

Ala Ala Glu Val Ala Val Glu Lys Gly Gly Ser Ser Val Val Ala Leu
        435                 440                 445

Gln Arg Phe Val Asp Met Val Val Ser
    450                 455

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaacatatgg aaggcgtcat acttc                                          25

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttttgatcat taatcacgag ttacggaatc                                     30

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaacatatgg aggacacgat tgttatc                                        27

<210> SEQ ID NO 17

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcatatgtc aatccctcgt ggccagaag                                    29

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaacatatgg aggacactat cgttctc                                      27

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttggatcctt aagaaaccac catatcaac                                    29

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggccaaacgc gccggagctg atgtaga                                      27

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agtgggtata ttcaagcctg t                                            21

<210> SEQ ID NO 22
<211> LENGTH: 1433
<212> TYPE: DNA
<213> ORGANISM: Sesamum indicum
<220> FEATURE:
<221> NAME/KEY: CDS
<222> LOCATION: (1)..(1371)

<400> SEQUENCE: 22 atg gaa gac acc gtt gtc ctc tac act tcg gca gag cac ttg aat tcc    48
Met Glu Asp Thr Val Val Leu Tyr Thr Ser Ala Glu His Leu Asn Ser
 1               5                  10                  15 atg tta gtg ctg gcc aaa ttc att agc aaa cat tat ccc tcc atc ccc    96
Met Leu Val Leu Ala Lys Phe Ile Ser Lys His Tyr Pro Ser Ile Pro
```

```
                    20                  25                  30
ctc cta atc ctt tgc tcc gcc ccc gag tcc gcc gcg gct tcc gtc gcc    144
Leu Leu Ile Leu Cys Ser Ala Pro Glu Ser Ala Ala Ala Ser Val Ala
             35                  40                  45 acc gtg cct tcc atc act tac cac cgc ctc cca cct ccc gct ctt cct    192
Thr Val Pro Ser Ile Thr Tyr His Arg Leu Pro Pro Pro Ala Leu Pro
 50                  55                  60 ccc aac ttg acc acc aat cct ctt gaa ctc tta ttc gaa ata cct cgt    240
Pro Asn Leu Thr Thr Asn Pro Leu Glu Leu Leu Phe Glu Ile Pro Arg
 65                  70                  75                  80 ctc aac aac cca aat gtt agc aaa gcc ctt caa gag atc tcc cag aag    288
Leu Asn Asn Pro Asn Val Ser Lys Ala Leu Gln Glu Ile Ser Gln Lys
                 85                  90                  95 tca aga atc aaa gca ttt gtc att gat ttc ttc tgc aat cca gtt ttt    336
Ser Arg Ile Lys Ala Phe Val Ile Asp Phe Phe Cys Asn Pro Val Phe
                100                 105                 110 gaa gtt tct aca ggc ttg aat ata ccc act tac ttc tac atc agc tcc    384
Glu Val Ser Thr Gly Leu Asn Ile Pro Thr Tyr Phe Tyr Ile Ser Ser
            115                 120                 125 ggc gcg ttt ggc ctt tgc ccc ttt ctg aat ttc ccc act atc gag gaa    432
Gly Ala Phe Gly Leu Cys Pro Phe Leu Asn Phe Pro Thr Ile Glu Glu
130                 135                 140 acc gtt cct gga gac ctt gct gac ttg aat gat ttt gtc gaa att cct    480
Thr Val Pro Gly Asp Leu Ala Asp Leu Asn Asp Phe Val Glu Ile Pro
145                 150                 155                 160 ggc tgc cca ccc gtt cac tca tca gat ttc ccc gag gct atg att cat    528
Gly Cys Pro Pro Val His Ser Ser Asp Phe Pro Glu Ala Met Ile His
                165                 170                 175 cgt aag agt aat atc tac aaa cat ttt atg gac gcc gca aga aac atg    576
Arg Lys Ser Asn Ile Tyr Lys His Phe Met Asp Ala Ala Arg Asn Met
                180                 185                 190 gca aaa tca acc gga aac ctg gta aac gca ttt gat gcg ctc gag ttt    624
Ala Lys Ser Thr Gly Asn Leu Val Asn Ala Phe Asp Ala Leu Glu Phe
            195                 200                 205 agg gct aag gaa gca ctg ata aac ggt ttg tgc att ccc aat gcg cca    672
Arg Ala Lys Glu Ala Leu Ile Asn Gly Leu Cys Ile Pro Asn Ala Pro
210                 215                 220 aca ccg cct gtt tac ttg gtt gga ccc tta gtt ggt gat agc aac cgt    720
Thr Pro Pro Val Tyr Leu Val Gly Pro Leu Val Gly Asp Ser Asn Arg
225                 230                 235                 240 aac aac ggc tgc ata cag cat gaa tgc ctg aag tgg ctt gat tcg cag    768
Asn Asn Gly Cys Ile Gln His Glu Cys Leu Lys Trp Leu Asp Ser Gln
                245                 250                 255 ccc agc aaa agc gtg att ttc ctc tgc ttc ggc agg agg ggc ttg ttt    816
Pro Ser Lys Ser Val Ile Phe Leu Cys Phe Gly Arg Arg Gly Leu Phe
                260                 265                 270 tcc gtt gaa cag ctt aaa gaa atg gcg ctt ggt ctg gaa aat agc ggc    864
Ser Val Glu Gln Leu Lys Glu Met Ala Leu Gly Leu Glu Asn Ser Gly
            275                 280                 285 tat aga ttt ctt tgg tcc gtg cgc agt cca ccg ggc aag cag aat tca    912
Tyr Arg Phe Leu Trp Ser Val Arg Ser Pro Pro Gly Lys Gln Asn Ser
290                 295                 300 gca gcg gcg gag cca gac ttg gat gag ctg cta cca aag ggt ttc ctg    960
Ala Ala Ala Glu Pro Asp Leu Asp Glu Leu Leu Pro Lys Gly Phe Leu
305                 310                 315                 320 gag aga act aaa gac agg ggc ttc ata att aag tca tgg gcg ccg cag   1008
Glu Arg Thr Lys Asp Arg Gly Phe Ile Ile Lys Ser Trp Ala Pro Gln
                325                 330                 335 acg gaa gtg ctg agt cac gat tcg gtg ggt ggg ttc gtg aca cac tgc   1056
Thr Glu Val Leu Ser His Asp Ser Val Gly Gly Phe Val Thr His Cys
```

```
                340             345             350
ggt agg agc tca att ctg gaa gcg gtg tcg ctg ggg gtg ccg atg atc   1104
Gly Arg Ser Ser Ile Leu Glu Ala Val Ser Leu Gly Val Pro Met Ile
        355                 360                 365 ggg tgg ccg ttg tac gcg gag cag agg atg aat cgg gtt ttc atg gtg   1152
Gly Trp Pro Leu Tyr Ala Glu Gln Arg Met Asn Arg Val Phe Met Val
370                 375                 380 gag gaa atg aag gtg gcg ctg cca tta gag gag acg gcg gat ggg tta   1200
Glu Glu Met Lys Val Ala Leu Pro Leu Glu Glu Thr Ala Asp Gly Leu
385                 390                 395                 400 gtg acg gcg gtt gag ttg gag aag cga gtc aga cag ttg atg gac tcc   1248
Val Thr Ala Val Glu Leu Glu Lys Arg Val Arg Gln Leu Met Asp Ser
                405                 410                 415 cag acg gga aga gct gtg cga cac cga gtg acc gaa ttg aaa agc tcc   1296
Gln Thr Gly Arg Ala Val Arg His Arg Val Thr Glu Leu Lys Ser Ser
            420                 425                 430 gct gcg gcg gcg gtg cgg aag aat gga tcg tcg cta gtg gcg ttg caa   1344
Ala Ala Ala Ala Val Arg Lys Asn Gly Ser Ser Leu Val Ala Leu Gln
        435                 440                 445 aat ttc att gcg tcg gtg act cgg gtt tgagtgatgt tattactcca         1391
Asn Phe Ile Ala Ser Val Thr Arg Val
450                 455 agtaataaaa tttaattacc gtgtaaaaaa aaaaaaaaaa aa                    1433

<210> SEQ ID NO 23
<211> LENGTH: 457
<212> TYPE: PRT
<213> ORGANISM: Sesamum indicum

<400> SEQUENCE: 23

Met Glu Asp Thr Val Val Leu Tyr Thr Ser Ala Glu His Leu Asn Ser
1               5                   10                  15

Met Leu Val Leu Ala Lys Phe Ile Ser Lys His Tyr Pro Ser Ile Pro
            20                  25                  30

Leu Leu Ile Leu Cys Ser Ala Pro Glu Ser Ala Ala Ala Ser Val Ala
        35                  40                  45

Thr Val Pro Ser Ile Thr Tyr His Arg Leu Pro Pro Pro Ala Leu Pro
    50                  55                  60

Pro Asn Leu Thr Thr Asn Pro Leu Glu Leu Leu Phe Glu Ile Pro Arg
65                  70                  75                  80

Leu Asn Asn Pro Asn Val Ser Lys Ala Leu Gln Glu Ile Ser Gln Lys
                85                  90                  95

Ser Arg Ile Lys Ala Phe Val Ile Asp Phe Phe Cys Asn Pro Val Phe
            100                 105                 110

Glu Val Ser Thr Gly Leu Asn Ile Pro Thr Tyr Phe Tyr Ile Ser Ser
        115                 120                 125

Gly Ala Phe Gly Leu Cys Pro Phe Leu Asn Phe Pro Thr Ile Glu Glu
    130                 135                 140

Thr Val Pro Gly Asp Leu Ala Asp Leu Asn Asp Phe Val Glu Ile Pro
145                 150                 155                 160

Gly Cys Pro Pro Val His Ser Ser Asp Phe Pro Glu Ala Met Ile His
                165                 170                 175

Arg Lys Ser Asn Ile Tyr Lys His Phe Met Asp Ala Ala Arg Asn Met
            180                 185                 190

Ala Lys Ser Thr Gly Asn Leu Val Asn Ala Phe Asp Ala Leu Glu Phe
        195                 200                 205

Arg Ala Lys Glu Ala Leu Ile Asn Gly Leu Cys Ile Pro Asn Ala Pro
```

-continued

```
                 210                 215                 220
Thr Pro Pro Val Tyr Leu Val Gly Pro Leu Val Gly Asp Ser Asn Arg
225                 230                 235                 240

Asn Asn Gly Cys Ile Gln His Glu Cys Leu Lys Trp Leu Asp Ser Gln
                245                 250                 255

Pro Ser Lys Ser Val Ile Phe Leu Cys Phe Gly Arg Arg Gly Leu Phe
            260                 265                 270

Ser Val Glu Gln Leu Lys Glu Met Ala Leu Gly Leu Glu Asn Ser Gly
        275                 280                 285

Tyr Arg Phe Leu Trp Ser Val Arg Ser Pro Pro Gly Lys Gln Asn Ser
290                 295                 300

Ala Ala Ala Glu Pro Asp Leu Asp Glu Leu Leu Pro Lys Gly Phe Leu
305                 310                 315                 320

Glu Arg Thr Lys Asp Arg Gly Phe Ile Ile Lys Ser Trp Ala Pro Gln
                325                 330                 335

Thr Glu Val Leu Ser His Asp Ser Val Gly Gly Phe Val Thr His Cys
            340                 345                 350

Gly Arg Ser Ser Ile Leu Glu Ala Val Ser Leu Gly Val Pro Met Ile
        355                 360                 365

Gly Trp Pro Leu Tyr Ala Glu Gln Arg Met Asn Arg Val Phe Met Val
370                 375                 380

Glu Glu Met Lys Val Ala Leu Pro Leu Glu Glu Thr Ala Asp Gly Leu
385                 390                 395                 400

Val Thr Ala Val Glu Leu Glu Lys Arg Val Arg Gln Leu Met Asp Ser
                405                 410                 415

Gln Thr Gly Arg Ala Val Arg His Arg Val Thr Glu Leu Lys Ser Ser
            420                 425                 430

Ala Ala Ala Ala Val Arg Lys Asn Gly Ser Ser Leu Val Ala Leu Gln
        435                 440                 445

Asn Phe Ile Ala Ser Val Thr Arg Val
    450                 455

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caccatatgg aagacaccgt tgtcctcta                                         29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggatcctaac atcactcaaa cccgagtca                                         29

<210> SEQ ID NO 26
<211> LENGTH: 441
<212> TYPE: PRT
<213> ORGANISM: Scutellaria baicalensis

<400> SEQUENCE: 26
```

```
Met Ala Val Leu Ala Lys Phe Ile Ser Lys Asn His Pro Ser Val Pro
1               5                   10                  15

Ile Ile Ile Ile Ser Asn Ala Pro Glu Ser Ala Ala Ser Val Ala
            20                  25                  30

Ala Ile Pro Ser Ile Ser Tyr His Arg Leu Pro Leu Pro Glu Ile Pro
            35                  40                  45

Pro Asp Met Thr Thr Asp Arg Val Glu Leu Phe Phe Glu Leu Pro Arg
    50                  55                  60

Leu Ser Asn Pro Asn Leu Leu Thr Ala Leu Gln Gln Ile Ser Gln Lys
65                  70                  75                  80

Thr Arg Ile Arg Ala Val Ile Leu Asp Phe Phe Cys Asn Ala Ala Phe
                85                  90                  95

Glu Val Pro Thr Ser Leu Asn Ile Pro Thr Tyr Tyr Tyr Phe Ser Ala
            100                 105                 110

Gly Thr Pro Thr Ala Ile Leu Thr Leu Tyr Phe Glu Thr Ile Asp Glu
            115                 120                 125

Thr Ile Pro Val Asp Leu Gln Asp Leu Asn Asp Tyr Val Asp Ile Pro
    130                 135                 140

Gly Leu Pro Pro Ile His Cys Leu Asp Ile Pro Val Ala Leu Ser Pro
145                 150                 155                 160

Arg Lys Ser Leu Val Tyr Lys Ser Ser Val Asp Ile Ser Lys Asn Leu
                165                 170                 175

Arg Arg Ser Ala Gly Ile Leu Val Asn Gly Phe Asp Ala Leu Glu Phe
            180                 185                 190

Arg Ala Ile Gly Ser His Ser Gln Arg Pro Met His Phe Lys Gly Pro
            195                 200                 205

Thr Pro Pro Val Tyr Phe Ile Gly Pro Leu Val Gly Asp Val Asp Thr
    210                 215                 220

Lys Ala Gly Ser Glu Glu His Glu Cys Leu Arg Trp Leu Asp Thr Gln
225                 230                 235                 240

Pro Ser Lys Ser Val Val Phe Leu Cys Phe Gly Arg Arg Gly Val Phe
                245                 250                 255

Ser Ala Lys Gln Leu Lys Glu Thr Ala Ala Leu Glu Asn Ser Gly
            260                 265                 270

His Arg Phe Leu Trp Ser Val Arg Asn Pro Pro Glu Leu Lys Lys Ala
            275                 280                 285

Thr Gly Ser Asp Glu Pro Asp Leu Asp Glu Leu Leu Pro Glu Gly Phe
    290                 295                 300

Leu Glu Arg Thr Lys Asp Arg Gly Phe Val Ile Lys Ser Trp Ala Pro
305                 310                 315                 320

Gln Lys Glu Val Leu Ala His Asp Ser Val Gly Gly Phe Val Thr His
                325                 330                 335

Cys Gly Arg Ser Ser Val Ser Glu Gly Val Trp Phe Gly Val Pro Met
            340                 345                 350

Ile Gly Trp Pro Val Asp Ala Glu Leu Arg Leu Asn Arg Ala Val Met
            355                 360                 365

Val Asp Asp Leu Gln Val Ala Leu Pro Leu Glu Glu Ala Gly Gly
    370                 375                 380

Phe Val Thr Ala Ala Glu Leu Glu Lys Arg Val Arg Glu Leu Met Glu
385                 390                 395                 400

Thr Lys Ala Gly Lys Ala Val Arg Gln Arg Val Thr Glu Leu Lys Leu
                405                 410                 415
```

```
Ser Ala Arg Ala Ala Val Ala Glu Asn Gly Ser Ser Leu Asn Asp Leu
        420                 425                 430

Lys Lys Phe Leu His Ala Thr Arg Asp
        435                 440
```